US006329510B1

(12) United States Patent
Qin et al.

(10) Patent No.: US 6,329,510 B1
(45) Date of Patent: Dec. 11, 2001

(54) ANTI-CCR1 ANTIBODIES AND METHODS OF USE THEREFOR

(75) Inventors: Shixin Qin, Lexington; Walter Newman, Boston; Nasim Kassam, Waltham, all of MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/239,938

(22) Filed: Jan. 29, 1999

(51) Int. Cl.$^7$ .................................................. C07K 16/28

(52) U.S. Cl. ................... 530/388.22; 424/143.1; 424/144.7

(58) Field of Search ...................... 424/143.1, 144.7; 530/388.22

(56) References Cited

U.S. PATENT DOCUMENTS

| | | | |
|---|---|---|---|
| 5,440,021 | 8/1995 | Chuntharapai et al. | 530/388.22 |
| 5,543,503 | 8/1996 | Chuntharapai et al. | 530/388.22 |
| 5,545,806 | 8/1996 | Lonberg et al. | 800/2 |
| 5,545,807 | 8/1996 | Surani et al. | 800/2 |
| 5,652,133 | 7/1997 | Murphy | 435/325 |
| 5,677,184 | 10/1997 | Onda et al. | 435/360 |

FOREIGN PATENT DOCUMENTS

| | | |
|---|---|---|
| 43 32 256 C1 | 3/1995 | (DE) . |
| WO 94/11504 | 5/1994 | (WO) . |
| WO 95/08576 | 3/1995 | (WO) . |
| WO 98/38167 | 9/1998 | (WO) . |
| WO 98/44953 | 10/1998 | (WO) . |
| WO 99/15666 | 4/1999 | (WO) . |

OTHER PUBLICATIONS

Chuntharapai et al. Generation of Monoclonal Antibodies to Chemokine Receptors. Methods in Enzymology 288:15–27, Oct. 1997.*

Osbourn, J., et al., "Directed selection of MIP–1α neutralizing CCR5 antibodies from a phage display human antibody library", *Nature Biotechnology*, 16: 778–781 (1998).

Sato, K., et al., "CC Chemokine Receptors, CCR–1 and CCR–3, are Potentially Involved in Antigen–Presenting Cell Function of Human Peripheral Blood Monocyte–Derived Dendritic Cells", *Blood* 93 (1):34–42 (1999).

Durig, J. et al., "Expression of Macrophage Inflammatory Protein–1α Receptors in Human CD34$^+$ Hematopoietic Cells and Their Modulation by Tumor Necrosis Factor–α and Interferon–γ", *Blood* 92(9):3073–3081 (1998).

Johnston, B. et al., "Chronic Inflammation Upregulates Chemokine Receptors and Induces Neutrophil Migration to Monocyte Chemoattractant Protein–1", *Journal of Clinical Investigation* 103(9):1269–1276 (1999).

Pease, James E., et al., "The N–terminal Extracellular Segments of the Chemokine Receptors CCR1 and CCR3 Are Determinants for MIP–1α and Eotaxin Binding, Respectively, but a Second Domain Is Essential for Efficient Receptor Activation", *The Journal of Biological Chemistry*, 273(32):19972–19976 (1988).

Su, Shao–bo, et al., "Determination of Expression of a C–C Chemokine Receptor, CC CKR1 on Leukocytes", 6th International Workshop and Conference on Human Leukocyte Differentiation Antigens, Kobe, Japan, Nov. 10–14, 1996, *Tissue Antigens*, 48(4–2):389 (1996) Abstract No. CR–1–07.

Su, Shao–bo, et al., "Selective Inhibition of BFU–E Proliferation by Macrophage Inflammatory Protein (MIP)–1α by Interacting Mainly with CCR1" (from *Nippon Neneki Gakkai Sokai Gakujutsu Shukai Kiroku*, 27:287 (1997) Abstract No. 2P76).

Su, Shao–bo, et al., "Inhibition of Immature Erythroid Progenitor Cell Proliferation by Macrophage Inflammatory Protein–1α by Interacting Mainly With a C–C Chemokine Receptor, CCR1", *Blood*, 90(2):605–611 (1997).

Murakami, Seishi, et al., "Human Hepatitis Virus X Gene Encodes a Regulatory Domain That Represses Transactivation of X Protein", *The Journal of Biological Chemistry*, 269(21):15118–15123 (1994).

Su, Shao–bo, et al., "Preparation of Specific Polyclonal Antibodies to a C–C Chemokine Receptor, CCR1, and Determination of CCR1 Expression on Various Types of Leukocytes", *Journal of Leukocyte Biology*, 60:658–666 (1996).

Sallusto, Federica, et al., "Rapid and Coordinated Switch in Chemokine Receptor Expression During Dendritic Cell Maturation", *Eur. J. Immunol.*, 28:2760–2769 (1998).

Neote, Kuldeep, et al., "Molecular Cloning, Functional Expression, and Signaling Characteristics of a C–C Chemokine Receptor", *Cell*, 72:415–425 (1993).

http://cytokine.rndsystems.com/search/mfs/02/subdoc/flow.html, "Flow Cytometry Kits for Cell Surface Staining" (1998).

http://cytokine.rndsystems.com/search/mfs/02/subdoc/anti.html, "Antibodies to Cytokines and Cytokine Receptors (A–H)" (1998).

Schall, Thomas J., et al., "Molecular Cloning and Expression of the Murine RANTES Cytokine: Structural and Functional Conservation Between Mouse and Man", *Eur. J. Immunol.*, 22:1477–1481 (1992).

(List continued on next page.)

*Primary Examiner*—John Ulm
(74) *Attorney, Agent, or Firm*—Hamilton, Brook, Smith & Reynolds, P.C.

(57) ABSTRACT

The present invention relates to an antibody or functional fragment thereof which binds to a mammalian (e.g., human) CC-chemokine receptor 1 (CCR1) or a portion of the receptor and blocks binding of a ligand to the receptor. The invention further relates to a method of inhibiting the interaction of a cell bearing mammalian CCR1 with a ligand thereof, and to use of the antibodies and fragments in research, therapeutic, prophylactic and diagnostic methods.

38 Claims, 13 Drawing Sheets

OTHER PUBLICATIONS

Forssmann, Ulf, et al., "CKβ8, A Novel CC Chemokine That Predominantly Acts on Monocytes", *FEBS Letters,* 408:211–216 (1997).

Gong, Xiaoqi, et al., "Monocyte Chemotactic Protein–2 (MCP–2) Uses CCR1 and CCR2B as Its Functional Receptors", *The Journal of Biological Chemistry,* 272(18):11682–11685 (1997).

Youn, Byung–S., "Molecular Cloning of Leukotactin–1: A Novel Human β–Chemokine, a Chemoattractant for Neutrophils, Monocytes, and Lymphocytes, and a Potent Agonist at CC Chemokine Receptors 1 and 3", *J. Immunol.,* 159:5201–5205 (1997).

Youn, Byung–S., et al., "Characterization of CKβ8 and CKβ8–1: Two Alternatively Spliced Forms of Human β–Chemokine, Chemoattractants for Neutrophils, Monocytes, and Lymphocytes, and Potent Agonists at CC Chemokine Receptor 1", *Blood,* 91(9):3118–3126 (1998).

Nomura, Hideki, et al., "Molecular Cloning of cDNAs Encoding a LD78 Receptor and Putative Leukocyte Chemotactic Peptide Receptors", *International Immunology,* 5(10):1239–1249 (1993).

Gao, Ji–Liang, et al., "Structure and Functional Expression of the Human Macrophage Inflammatory Proteins 1α/RANTES Receptor", *The Journal of Experimental Medicine,* 177:1421–1427 (1993).

Bonecchi, Rafaella, et al., "Up–Regulation of CCR1 and CCR3 and Induction of Chemotaxis to CC Chemokines by INF–γ in Human Neutrophils", *The Journal of Immunology,* 162(1):474–479 (1999).

U.S. Patent Application Serial No. 09/239,283, filed Jan. 29, 1999, entitled "Methods for Preventing Graft Rejection and Ischemia–Reperfusion Injury" by Wayne W. Hancock.

U.S. Patent Application Serial No. 09/240,253, filed Jan. 29, 1999, entitled "Method of Treating Demyelinating Inflammatory Disease Using CCR1 Antagonists" by James B. Rottman and Wayne W. Hancock.

Förster, R., et al., "A general method for screening mAbs specific for G–protein coupled receptors as exemplified by using epitope tagged BLR1–transfected 293 cells and solid–phase cell ELISA," *Biochemical and Biophysical Research Communications* 196(3):1496–1503 (1993).

Jakobovits, A., et al., "Analysis of homozygous mutant chimeric mice: Deletion of the immunoglobulin heavy–chain joining region blocks B–cell development and antibody production", *Genetics,* 90: 2551–2555 (1993).

Jakobovits, A., et al., "Germ–line transmission and expression of a human–derived yeast artificial chromosome", *Nature,* 362: 255–258 (1993).

\* cited by examiner

Chemokine (nM)

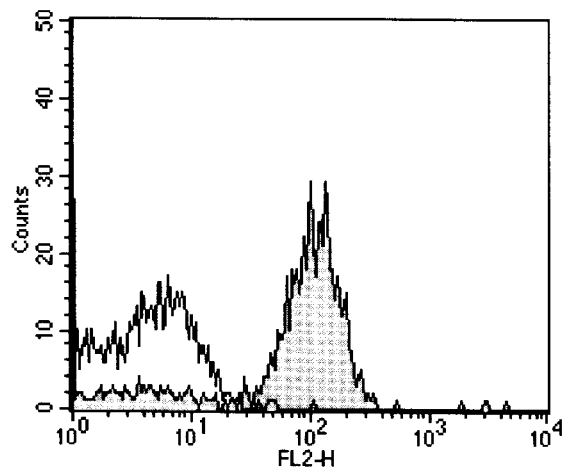

FIG. 11

PROTEIN SEQUENCE OF HUMAN CCR1

```
  1     metpnttedy   dtttefdygd   atpcqkvner   afgaqlllppl   yslvfviglv   gnilvvlvlv
              N-Terminal                                     |——> TM1                <——|

61     qykrlknmts   iyllnlaisd   llflftlpfw   idyklkddwv   fgdamckils   gfyytglyse
             |——> TM2                         <——| EC1                  |——> TM3

121     iffiilltid   rylaivhavf   alrartvtfg   vitsiiiwal   ailasmpgly   fsktqwefth
        TM3 <——|                              |——> TM4                  <——|       EC2

181     htcslhfphe   slrewklfqa   lklnlfglvl   pllvmiicyt   giikillrrp   nekkskavrl
         EC2                                  |——> TM5                  <——|        |-

241     ifvimiiffl   fwtpynltil   isvfqdflft   heceqsrhld   lavqvtevia   ythccvnpvi
        —>     TM6             <——|            EC3                     |——> TM7          <-

301     yafygerfrk   ylrqlfhrrv   avhlvkwlpf   lsvdrlervs   stspstgehe   lsagf
        ——|                       C-Tail
```

TM = transmembrane region
EC = extracellular domain

FIG. 12

ANTI-CCR1 ANTIBODIES AND METHODS OF USE THEREFOR

BACKGROUND OF THE INVENTION

Over the last decade, chemokines have emerged as key mediators of inflammation as a result of their numerous pro inflammatory activities which affect virtually every leukocyte type. More recently, chemokines have been recognized as a critical component of basal leukocyte trafficking essential for normal immune surveillance and response, as well as for several other functions in hematopoiesis, angiogenesis, control of viral infection, and T cell differentiation (Baggiolini et al., *Ann Rev. Immunol.* 15:675 (1997); Zou et al., *Nature* 393.595 (1998); Tachibana et al., *Nature* 393:591 (1998)). This diverse array of biological activities, including mediation of a range of pro-inflammatory effects on leukocytes, such as triggering of chemotaxis, degranulation, synthesis of lipid mediators, and integrin activation, together with their critical role in the initiation and maintenance inflammatory diseases, and the recent identification of certain chemokine receptors as co-receptors for HIV-1 entry, have made chemokines and chemokine receptors an attractive new set of therapeutic targets.

Members of the chemokine family are produced and secreted by many cell types in response to early inflammatory mediators such as IL-1β or TNFα. The chemokine superfamily comprises two main branches: the α-chemokines (or CXC chemokines) which are characterized by a single amino acid separating the first 2 cysteines, and the β-chemokines (CC chemokines), which contain two adjacent cysteines. The α-chemokine branch includes proteins such as IL-8, neutrophil activating peptide-2 (NAP-2), melanoma growth stimulatory activity (MGSA/gro or GROα), and ENA-78, each of which have attracting and activating effects predominantly on neutrophils. The members of the β-chemokine branch affect other cell types such as monocytes, lymphocytes, basophils, and cosinophils (Oppenheim, J. J. et al., *Annu. Rev. Immunol.*, 9:617–648 (1991); Baggiolini, M., et al., *Adv. Immunol.*, 55:97–179 (1994); Miller and Krangel, *Crit. Rev. Immunol.*, 12:17–46 (1992); Jose, P. J., et al., *J. Exp. Med.*, 179:881–118 (1994); Ponath, P. D., et al., *J. Clin. Invest.*, 97:604–612 (1996)), and include proteins such as monocyte chemotactic proteins 1–4 (MCP-1, MCP-2, MCP-3, and MCP-4), RANTES, macrophage inflammatory proteins (MIP-1α, MIP-1β), thymus and activation-regulated chemokine (TARC) and macrophage-derived chemokine (MDC).

Chemokines bind to 7 transmembrane spanning G protein-coupled receptors (Murphy, P. M., *Annu. Rev. Immunol.*, 12:593–633 (1994)). A number of β chemokine receptors (CCR1 -CCR10) have been identified to date, and the search for additional chemokine receptors is the subject of active research (Baggiolini, *Nature* 392:565–568 (1998)). Chemokine receptor CCR1 was identified by Nomura et al., (*Int. Immunol.* 5:1239–1249 (1993); Neotc et ia., (*Cell* 72:415–425 (1993)) and Gao et al., (*J. Exp. Med.* 177:1421–1427 (1993)). CCR1 was originally found to signal in response to MIP-1α and RANTES, but more recently has also been shown to signal in response to additional chemokine ligands.

The selective recruitment of leukocyte subsets to sites of inflammation and the ordered trafficking of leukocytes through the circulation, tissues, lymphatic system and secondary lymphoid organs is controlled in part by the differential expression of chemokine receptors on subsets of cells. Such expression patterns would seem to ensure that a functionally related group of leukocytes can coordinately respond to a specific set of chemokines induced by a given stimulus. However, most leukocytes express several chemokine receptors, many with complex and promiscuous ligand interactions. For T cells, PCR or Northern blotting indicates that the known receptors for CC chemokines are expressed on subsets of T cells. Delineating exactly which subsets express particular receptors is an area of intense study, because chemokine receptor expression may explain the localization or migration of various cell types, such as TH1 or TH2 T cells or tissue homing subsets. It may also determine which T cells are infected with different strains of HIV-1. This makes elucidating the normal immune function for a specific receptor on a given cell type and determining the relevance to initiation and progression of disease difficult, especially since specific antibodies are not available for many chemokine receptors.

SUMMARY OF THE INVENTION

CCR1 was the first chemokine receptor shown to interact with C—C (β) chemokines. Originally identified as a MIP-1α/RANTES receptor, more recent studies have demonstrated that CCR1 may have as many as 6 or more β chemokine ligands. Work described herein characterizes the expression of CCR1 by flow cytometry and assesses iii vitro the relative functional contribution of this receptor oil human leukocytes using a blocking monoclonal antibody. In peripheral blood, all monocytes express high levels of CCR1, and monocyte responses to both MIP-1α and RANTES can be completely blocked by the anti-CCR1 mAb 2D4. CCR1 is expressed on a small percentage of CD45RO+ CD26+ T cells, suggesting that it marks a subset of memory T cells. In contrast with chemokine receptors CCR5 and CXCR3, which are upregulated on activated T cells, CCR1 expression is diminished upon T cell activation. Neutrophils express low levels of CCR1 and show a weak response to MIP-1α in $[Ca^{2+}]_i$ mobilization assays, which can be inhibited by the anti-CCR1 mAb 2D4. The expression of CCR1 on cosinophils is extremely variable among individuals, ranging from >90% positive to completely negative. The expression pattern of CCR1 suggests that it is involved in a broad range of immunological activities, playing a major role in monocyte and cosinophil function, as well as in the function of a subset of T lymphocytes.

The present invention relates to an antibody (immunoglobulin) or functional fragment thereof (e.g., an antigen-binding fragment) which binds to a mammalian CC-chemokine receptor 1 (also referred to as CCR1 or CKR-1) or portion of the receptor (anti-CCR1). In one embodiment, the antibody of the present invention or fragment thereof has specificity for human CCR1 or a portion thereof. In another embodiment, the antibody or fragment of the invention inhibits (reduces or prevents) binding of a ligand (e.g., MIP-1α, RANTES, MCP-2, MCP-3, leukotactin-1, HCC-1 or MPIF) to the receptor and inhibits one or more functions associated with binding of the ligand to the receptor (e.g., leukocyte trafficking). In a preferred embodiment, the ligand is MIP-1α or RANTES. For example, as described herein, antibodies and fragments thereof of the present invention which bind human CCR1 or a portion thereof, can block binding of a chemokine (e.g., MIP-1α, RANTES, MCP-2, MCP-3, leukotactin-1, HCC-1, or MPIF) to the receptor and inhibit function associated with binding of the chemokine to the receptor.

In a preferred embodiment, the antibody of the invention or fragment thereof has the same or similar epitopic specificity as monoclonal antibody (mAb) LS125-2D4 (2D4). For example, the antibody or fragment thereof can have epitopic specificity for the second extracellular loop of CCR1, such as a portion of CCR1 from about amino acid 171 to about amino acid 205. In one embodiment, the antibody is monoclonal antibody 2D4 or an antibody which can compete with 2D4 for binding to human CCR1 or a portion of human CCR1. Functional fragments of the foregoing antibodies are also envisioned.

In another embodiment, the antibody or fragment thereof binds CCR1 with an affinity of greater than about $5 \times 10^{-8}$ M, and more preferably at least about $5 \times 10^{-9}$ M. In a further embodiment, the antibody of the invention or fragment thereof inhibits chemokine binding to CCR1, preferably with an $IC_{50}$ of less than about 10 μg/ml, more preferably less than about 5 μg/ml, and more preferably less than about 1.0 μg/ml. In one embodiment, the antibody of the invention or fragment thereof inhibits MIP-1α binding to CCR1 with an $IC_{50}$ of about 0.5 μg/ml. In another embodiment, the antibody of the invention or fragment thereof inbits RANTES binding to CCR1 with an $IC_{50}$ of about 0.7 μg/ml. In a further embodiment of the invention, the antibody or fragment thereof inhibits of chemokine-induced (c.g., MIP-1α, RANTES- or HCC-1-induced) chemotaxis of cells (e.g., CCR1-bearing cells), preferably at less than about 50 μg/ml, more preferably at less than about 20 μg/ml, and even more preferably at less than about 10 μg/ml. It is envisioned that any of the antibodies or fragments described herein can be used in the methods described herein.

The present invention also relates to an antibody or functional fragment thereof (e.g., an antigen-binding fragment) which binds to a mammalian CCR1 or portion of the receptor and provides increased fluorescent staining intensity of CCR1 or compositions comprising CCR1 relative to other anti-CCR1 antibodies. In one embodiment, the antibody is monoclonal antibody 2D4 or an antibody which can compete with 2D4 for binding to human CCR1 or a portion of human CCR1.

The present invention further relates to a method of inhibiting the interaction of a cell bearing mammalian (e.g., human, non-human primate or murine) CCR1 with a ligand thereof, comprising contacting the cell with an effective amount of an antibody or functional fragment thereof which binds to a mammalian CCR1 or a portion of CCR1. Suitable cells include granulocytes, leukocytes, such as monocytes, macrophages, basophils and eosinophils, mast cells, and lymphocytes including T cells (e.g., CD8+ cells, CD4+ cells, CD26+ cells, CD25+ cells, CD45RO+ cells) such as Th1 and Th2 cells, and other cells expressing CCR1, such as a recombinant cell expressing CCR1 or portion thereof (e.g., transfected cells). In a particular embodiment, the antibody is 2D4 or an antibody which can compete with 2D4 for binding to human CCR1 or a portion of human CCR1.

Another embodiment of the invention relates to a method of inhibiting the interaction of a cell bearing mammalian CCR1 with a chemokine, comprising contacting said cell with an effective amount of an antibody or functional fragment thereof which binds to CCR1 or a portion of said receptor. In one embodiment of the method, the antibody or functional fragment thereof is any one or more of 2D4, an antigen-binding fragment of 2D4 or an antibody or fragment thereof having an epitopic specificity which is the same as or similar to that of 2D4. Furthermore, the invention relates to a method of inhibiting a function associated with binding of a chemokine to CCR1, comprising administering an effective amount of an antibody or functional fragment thereof which binds to mammalian CCR1 or a portion of said receptor. In one aspect of the method, the antibody or functional fragment thereof is any one or more of 2D4, an antigen-binding fragment of 2D4, or an antibody or fragment thereof having an epitopic specificity which is the same as or similar to that of 2D4.

Another aspect of the invention is a method of identifying expression of a mammalian CCR1 or portion of the receptor by a cell. According to the method, a composition comprising a cell or fraction thereof (e.g., a membrane fraction) is contacted with an antibody or functional fragment thereof (e.g., 2D4) which binds to a mammalian CCR1 protein or portion of the receptor under conditions appropriate for binding of the antibody thereto, and the formation of a complex between said antibody or fragment and said protein or portion thereof is detected. Detection of the complex, directly or indirectly, indicates the presence of the receptor or portion thereof on the cell or fraction thereof. The present invention also relates to a kit for use in detecting the presence of CCR1 or a portion thereof in a biological sample, comprising an antibody or functional fragment thereof which binds to a mammalian CCR1 or a portion of said receptor, and one or more ancillary reagents suitable for detecting the presence of a complex between said antibody or fragment and said protein or portion thereof.

Also encompassed by the present invention are methods of identifying additional ligands or other substances which bind a mammalian CCR1 protein, including inhibitors and/or promoters of mammalian CCR1 function. For example, agents having the same or a similar binding specificity as that of an antibody of the present invention or functional fragment thereof can be identified by a competition assay with said antibody or fragment. Thus, the present invention also encompasses methods of identifying ligands or other substances which bind the CCR1 receptor, including inhibitors (e.g., antagonists) or promoters (e.g., agonists) of receptor function. In one embodiment, cells which naturally express CCR1 receptor protein or suitable host cells which have been engineered to express a CCR1 receptor or variant encoded by a nucleic acid introduced into said cells are used in an assay to identify and assess the efficacy of ligands, inhibitors or promoters of receptor function. Such cells are also useful in assessing the function of the expressed receptor protein or polypeptide.

Thus, the invention also relates to a method of detecting or identifying an agent which binds a mammalian CCR1 or ligand binding variant thereof, comprising combining an agent to be tested, an antibody or antigen-binding fragment of the present invention (e.g., monoclonal antibody 2D4, an antibody having an epitopic specificity which is the same as or similar to that of 2D4, antigen-binding fragments of 2D4) and a composition comprising a mammalian CCR1 protein or a ligand binding variant thereof. The foregoing components can be combined under conditions suitable for binding of the antibody or antigen-binding fragment to mammalian CCR1 protein or a ligand binding variant thereof, and binding of the antibody or fragment to the mammalian CCR1 protein or ligand binding variant is detected or measured, either directly or indirectly, according to methods described herein or other suitable methods. A decrease in the amount of complex formed relative to a suitable control (e.g., in the absence of the agent to be tested) is indicative that the agent binds said receptor or variant. The composition comprising a mammalian CCR1 protein or a ligand binding variant thereof can be a membrane fraction of a cell bearing recombinant CCR1 protein or ligand binding variant thereof. The antibody or fragment thereof can be labeled with a label such as a radioisotope, spin label, antigen label, enzyme label, fluorescent group and chemiluminescent group. These and similar assays can be used to detect agents, including ligands (e.g., chemokines which interact with CCR1) or other substances, including inhibitors or promoters of receptor function, which can bind CCR1 and compete with the antibodies described herein for binding to the receptor.

According to the present invention, ligands, inhibitors or promoters of receptor function can be identified in a suitable assay, and further assessed for therapeutic effect. Inhibitors of receptor function can be used to inhibit (reduce or prevent) receptor activity, and ligands and/or promoters can be used to induce (trigger or enhance) normal receptor function where indicated. These ligands, inhibitors and promoters can be used to treat inflammatory diseases, autoimmune diseases, atherosclerosis, and graft rejection, or HIV infection, for example, in a method comprising administering an inhibitor of receptor function (e.g., chemokine binding or HIV binding) to an individual (e.g., a mammal, such as a human). These ligands, inhibitors and promoters can also be used in a method of stimulating receptor function by administering a novel ligand or promoter to an individual, providing a new approach to selective stimulation of leukocyte function, which is useful, for example, in the treatment of infectious diseases and cancer.

The present invention also encompasses a method of inhibiting leukocyte trafficking in a patient, comprising administering to the patient an effective amount of an antibody or functional fragment thereof which binds to a mammalian CCR1 or portion of said receptor and inhibits function associated with binding of a ligand to the receptor.

The present invention also relates to a method of inhibiting or treating CCR1-mediated disorders, such as inflammatory disorders, comprising administering to a patient an effective amount of an antibody or functional fragment thereof which binds to a mammalian CCR1 or portion of said receptor and inhibits CCR1 -mediated function.

The present invention further relates to an antibody or fragment thereof as described herein (e.g., monoclonal antibody 2D4, an antigen-binding fragment of 2D4, an antibody having an epitopic specificity which is the same as or similar to that of 2D4) for use in therapy (including prophylaxis) or diagnosis, and to the use of such an antibody or fragment for the manufacture of a medicament for the treatment of a CCR1-mediated disorder, or other disease or inflammatory condition as described herein.

BRIEF DESCRIPTION OF THE DRAWINGS

FIG. 1A shows the results when monoclonal antibody 2D4 was used to stain a variety of CC chemokine receptor transfectants expressed on the L1-2 parental cell line. Only CCR1 -transfected cells were positively stained. FIG. 1B is a graph showing the results when CCR1 -transfected cells were used in ligand binding assays in the presence of increasing concentrations of monoclonal antibody 2D4. The total binding was 11574±1355 cpm for MIP-1α and 1734±118 for RANTES.

FIG. 2A is a histogram of flow cytometry showing monocyte expression of CCR1. Normal human PBMC were stained with an irrelevant mouse IgG1 antibody (dotted line) and monoclonal antibody 2D4 (solid line). Monocytes were gated by forward and side scatters. FIG. 2B shows monocyte intracellular calcium mobilization after chemokine stimulation. Human PBMC were loaded with Fluo-3 and stimulated with 20 nM of MIP-1α, RANTES, IL-8 or 100 nM of HCC-1 as indicated by arrow heads. When antibody 2D4 was used, 50 μg/ml 2D4 was added just before the stimulation.

FIG. 3A shows the results when normal human PBMC were stained with 2D4 and monoclonal antibodies specific for T cells (CD3) or B cells (CD19). FIG. 3B shows CCR1 expression on T cell subsets. The plots shown were first gated on CD3+ cells, then analyzed for CCR1 versus CD26, CD45RO, CXCR3 and CCR5.

FIG. 5A shows the results when T cells were stimulated in the absence of INFα. FIG. 5B shows the results when T cells were cultured in the presence of IFNα. Migrated cells were counted by flow cytometry. In this experiment, the counts of total migration of CD3 blasts without IFNα were 3155, 2683 and 5483 for MIP-1α, MIP-1β and RANTES, respectively, with a background of 246. The total migration of IFNA treated cells were 11352, 6542 and 12136 for MIP-1α, MIP-1β and RANTES, respectively, with a background of 612. The data are representative of three experiments giving similar results.

FIG. 11 is a fluorescence plot illustrating the expression of CCR1 on human basophils. Human blood was stained with anti-CCR1, and basophils were identified by double staining with anti-IgE and gated by forward and side scatters. Anti-CCR1 2D4 staining is represented by shading. The control mouse IgG1 staining is represented by solid lines.

FIG. 12 depicts the amino acid sequence (SEQ ID NO. 1) of human CCR1. The predicted N-terminal, transmembrane (TM), extracellular (EC) and C-terminal portions are indicated.

DETAILED DESCRIPTION OF THE INVENTION

Figure 1A:
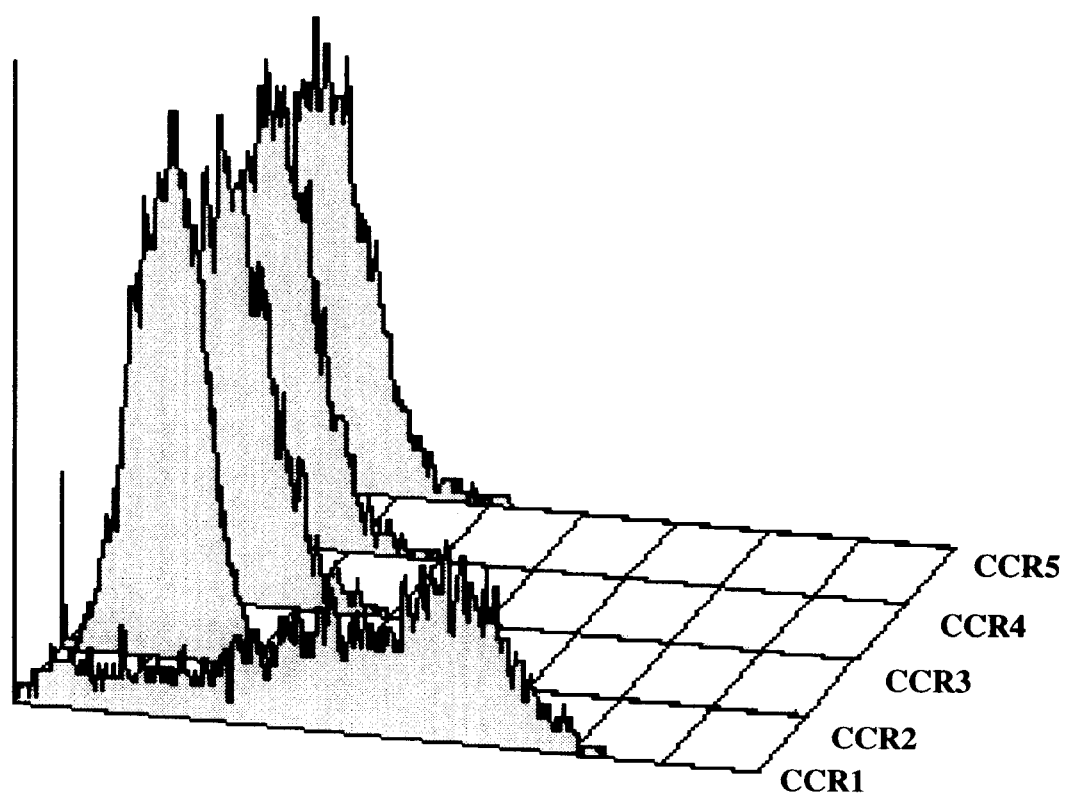
FIGS. 1A and 1B show the specific binding of monoclonal antibody 2D4 to CCR1.

The first C-C chemokine receptor identified, CCR1, was originally described as a MIP-1α/RANTES receptor. Since those reports, however, CCR1 has been shown to interact with a number of β chemokines, including MIP-1α, RANTES, MCP-2, MCP-3, leukotactin-1, HCC-1, and MPIF (Schall et al., *Eur. J. Immunol.* 22:1477 (1992); Forssmann et al., *FEBS Lett.* 408:211 (1997); Gong et al., *J. Biol. Chem.* 272:11682 (1997); Gong et al., *J. Biol. Chem.* 272:11682 (1997); Youn et al., *J. Immunol.* 159:5201 (1997); and Youn et al., *Blood* 91:3118 (1998)). Leukotactin-1 is also known as HCC-2 or MIP-1δ, HCC-1 is also known as Ckβ1 or MIP-1γ, and MPIF is also known as CKβ8 or MIP-3. Most of these chemokines are also reported as functional ligands for other chemokine receptors, such as CCR2 (Combadicre et al., *J. Biol. Chem.* 270:29671 (1995)), CCR3 (Ponath et al., *J. Exp. Med.* 183:2437 (1996)) and CCR5 (Samson et al., *Biochemistry* 35:3362 (1996), Raport et al., *J. Biol. Chem.* 271:17161 (1996)), with expression patterns overlapping that of CCR1. CCR1 mRNA has been detected in T cells (Loetscher et al., *J. Exp. Med.* 184:569 (1996)), B cells (Gao et al., *J. Exp. Med.* 177:1421 (1993)), basophils (Uguccioni et al., *J. Clin. Invest.* 100:1137 (1997)), eosinophils (Post et al., *J. immunol.* 155:5299 (1995)), monocytes and granulocytes (Nomura et al., *Int. Immunol.* 5:1239 (1993)), as well as dendritic cells (Sozzani et al., *J. Immunol.* 161:1083 (1998)), and all have been shown to be functionally responsive to CCR1 ligands.

Targeted disruption of CCR1 in mice has provided some insights into the role of this receptor in normal immune function and disease pathology. In one study (Gao et al., *J. Exp. Med.* 185:1959 (1997)), CCR1 −/− mice showed abnonnal steady-state and induced trafficking of myeloid progenitors from bone marrow to blood and spleen, accelerated mortality upon challenge with *Aspergillus fumigatus* likely due to impaired neutrophil function, diminished granulomatous inflammatory responses and altered Th1/Th2 cytokine balance. A separate report (Lu et al., *J. Exp. Med.* 187:601 (1998)) linked CCR1 to respiratory distress syndrome secondary to acute pancreatitis in mice, attributable to reduced intrapancreatic sequestration of neutrophils in the CCR1 knock-out animals.

Several studies have demonstrated in viva functions for MIP-1α and RANTES, the two most thoroughly studied CCR1 ligands. The importance of MIP-1α to both T cell-dependent and NK-dependent viral clearance has been demonstrated with MIP-1α knock-out mice (Cook et al., *Science* 269:1583 (1995)). The use of neutralizing antisera against MIP-1α and RANTES in rodent models of airway inflammation (Standiford et al., *J. Immunol.* 155:1515 (1995)), experimental allergic encephalomyelitis (EAE) (Karpus et al., *J. Immunol.* 155:5003 (1995)) and arthritis (Barnes et al., *J. Clin. Invest.* 101:2910 (1998)) suggests a role for these ligands in a range of inflammatory diseases. However, because MIP-1α and RANTES are ligands for CCR1, CCR3, and CCR5 in the mouse, the role of these individual receptors in these models and their validation as anti-inflammatory drug targets remains unclear.

As a step toward understanding the function of CCR1 in humans, a monoclonal antibody (mAb) against this receptor has been produced as described herein and used to characterize the expression and functions of CCR1 on human leukocytes. Inhibition of CCR1 ligand activities ini vitro by receptor blockade with the mAb support and confirm the results of flow cytometry. These data demonstrate that the expression and regulation of CCR1 is distinct from other C-C chemokine receptors such as CCR3 and CCR5, which share some common ligands, and provide further evidence for a complex and multifaceted chemokine-receptor system.

Chemokines and their receptors constitute an important component in the regulation of directed leukocyte migration. During an inflammatory response, chemokines are produced locally which attract various leukocytes bearing the corresponding receptors. While the spectrum of chemokines expressed at the lesion can differentially attract certain inflammatory cells, selectivity and variation in chemokine receptor expression on leukocytes provides further regulation to ensure appropriate cell recruitment to given stimuli. As the number of identified and characterized chemokine receptors continues to grow, it is becoming increasingly clear that cells selectively express several receptors which may identify, mark, or otherwise characterize functional subsets of leukocytes such as Th1 and Th2, naive and memory, activated and quiescent T cells. Because several chemokine receptors arc co-expressed on individual cells, it has been difficult to validate the role of a specific receptor in the initiation and progression of disease or, for that matter, in normal immune function. The expression pattern of CCR1 was assessed as described herein, and the functional contribution of this receptor to normal immune function was explored with anti-CCR1 mAb 2D4.

T cells, especially activated T cells, demonstrate chemotactic responses to a number of CC chemokines, including MCP-1, RANTES, MIP-1α, MIP-1β and CXC chemokines such as IP-10, MIG and ITAC. Increased expression of CCR2 (Qin el al., *Eur. J. Immunol.* 26:640 (1996)), CCR5 and CXCR3 (Qin et al., *J. Clin. Invest.* 101:746 (1998)) has been reported on activated T cells, which correlated with increased chemotactic activities to their ligands. Recent studies also described increased CCR1 mRNA from activated T cells (Sallusto et al., *J. Exp. Med.* 187:875 (1998)). Although a small population of resting T cells has been identified which express CCR1 in peripheral blood, significant CCR1 expression on the surface of T cells by anti-CD3 and IL-2 stimulation has not been identified. It is possible that there are post-transcriptional or post-translational mechanisms that control surface expression of CCR1. Alternatively, CCR1 might be down regulated by other cytokines produced during T cell activation, as has been reported in TNFα-induced shedding of CXCR2 from neutrophils (Asagoc et al., *J. Immunol.* 160:4518 (1998)). This data was consistent with previously reported work on anti-CCR5 mAbs (Wu et al., *J. Exp. Med.* 186:1373 (1997)) that most of the MIP-1α and RANTES effects on activated T cells appear to be through CCR5.

The fact that a CCR1 positive T cell population could be expanded under particular activation conditions, such as the IFNα treatment described herein, suggests that CCR1 may be involved in T cell responses to a distinct and perhaps more specific set of stimuli than either CCR5 or CXCR3, for example. IFNα is an important cytokine in host defense against viral infection and has been found to induce MIP-1α production by human PBMC (Bug et al., *Exp. Hematol.* 26:117 (1998)). Moreover, studies with MIP-1α deficient mice show impaired T cell inflammatory responses associated with infection by several viruses, including resistance to Coxsackie virus-induced myocarditis and reduced pneumonitis associated with influenza virus, as well as resistance to herpes simplex virus type 1 associated with influenza fvirus, as well as *Virol.* 72:3705 (1998)).

In addition to lymphocytes, monocytes also respond to C-C chemokines. It is shown herein by receptor blockade with mAb 2D4 that monocyte responses to MIP-1α and RANTES, as well as to HCC-1, appear to be entirely CCR1-dependent. Thus far the only other major C-C chemokine receptor found on human monocytes is CCR2. Given the role the monocyte/macrophage lineage may play as antigen presenting cells, and the findings that monocyte-derived dendritic cells express CCR1 (Sozzani et al., *J Immunol.* 161:1083 (1998)), this receptor and its ligands may play important roles in specific immune responses by regulating the migration of antigen presenting cells.

A number of studies have demonstrated the importance of CCR1 in rodent granulocyte migration. However, the expression and function of CCR1 on human granulocytes has remained unclear. With the specific mAb 2D4 described herein, CCR1 was detected on the majority of granulocytes. On eosinophils, the expression of CCR1 was highly variable among donors, in contrast to CCR3 which was always expressed at uniformly high levels.

Although CCR1 was found to be expressed on neutrophils, significant chemotactic response of these cells to CCR1 ligands MIP-1α RANTES or MPIF was not observed. The inability of neutrophils to migrate to CCR1 ligands could be due to the low density of receptor on the cell surface, as indicated by weak immunostaining, the lack of a signal transduction pathway component, or the lack of adhesion molecules. Similarly, it was observed that with resting T cells, about 30–40% of peripheral blood T cells express CXCR3 but fail to migrate in response to IP-10 or MIG unless activated with anti-CD3 and IL-2 (Qin et al., *J. Clin. Invest.* 101:746 (1998)). Alternatively, the results may suggest that chemotaxis is not the primary function of CCR1 on neutrophils. In fact, evidence for differential function of chemokine receptors has been described in neutrophils where IL-8 engagement of CXCR1, but not CXCR2, resulted in activation of NADPH oxidase and phospholipase D, while both receptors functioned in chemotaxis and elastase release (Jones et al., *Proc. Natl. Acad. Sci. USA*, 93:6682 (1996)). The lack of neutrophil chemotactic activity to CCR1 ligands is consistent with two previous reports which were also unable to detect neutrophil migration to MIP-1α (McColl et al., *J. Immunol.* 150:4550 (1993)) or MPIF (Forssmann et al., *FEBS Lett.* 408:211 (1997)), but in disagreement with other studies which found MPIF was chemotactic for neutrophils (Patel et al., *J. Exp. Med.* 185:1163 (1997)). About 10% of neutrophils responded to MIP-1α or MPIF stimulation with intracellular $Ca^{2+}$ mobilization, which was shown to be mediated by CCR1, as 2D4 could completely block the response. The observed $[Ca^{2+}]_i$ flux was not due to contaminating eosinophils, since cosinophils from these donors constitute less than 3% of total granulocytes, and is consistent with previous reports which found both MIP-1α and MPIF stimulated a $[Ca^{2+}]_i$ flux in neutrophils.

The expression of CCR1 on various leukocytes reported herein utilizing the anti-CCR1 mAb 2D4 is in marked contrast to a previous report using polyclonal antisera raised against a CCR1 N-terminal peptide-GST fusion protein (Su el al., *J. Leukoc. Biol.* 60:658 (1996)). It is shown herein that mAb 2D4 detected CCR1 expression on almost all monocytes, and Su et al. report that their polyclonal antisera detected CCR1 expression on monocytes. However the 2D4 mAb detected CCR1 expression only on discrete subpopulation of T cells; in contrast Su el al. report that the antisera stained >80% of CD3+ from peripheral blood. 2D4 also detected a discrete subpopulation of B cells (approximately 1–5%), while Su et al report that the antisera did not detect CCR1 expression on B cells, cosinophils or neutrophils. 2D4 not only detected this expression by flow cytometry but was able to functionally block MIP-1α-mediated chemotaxis and $Ca^{2+}$ flux in these cells, confirming the authenticity of staining and indicating that CCR1 is the predominant, if not the only, MIP-1α receptor on granulocytes. The significant discrepancy in staining profiles between the 2D4 mAb and the rabbit polyclonal antisera may be due to the different epitopes recognized by the reagents, as the rabbit polyclonal is reported to recognize epitopes in the $NH_2$-terminal domain, and 2D4 recognizes the second extracellular loop. Poor sensitivity resulting from low titre of antibodies recognizing native epitopes, as well as low affinity antibodies in the antisera, may explain the lack of detection of CCR1 on B cells, cosinophils, and neutrophils with the rabbit polyclonal antisera. Su et al. report that the antisera inhibited less than 50% of monocyte chemotaxis at 100 μg/ml, while 2D4 showed 100% inhibition at 50 μg/ml. However, the discrepancy in identification of T cell expression between the two reagents likely results from different epitope accessibility on the different cell types.

The ligands of CCR1 include MIP-1α, RANTES and MCP-3, which are also shared by other receptors, e.g. CCR3 interacts with MIP-α and RANTES as well as eotaxin, and CCR5 interacts with MIP-1α and RANTES as well as MIP-1β. This seeming redundancy may be necessary if the distribution of receptors for these ligands is considered. CCR3 is predominantly expressed on cosinophils, basophils and subsets of T cells but not on neutrophils or monocytes, CCR5 is expressed mostly on T cells, especially activated T cells. Work described herein shows that CCR1 could be found on all monocytes, the majority of granulocytes, including basophils, and a subpopulation of T cells. Furthermore, CCR1 expression on cosinophils and T cells appeared to be actively regulated. Therefore, each receptor has its own distinct population of host cells which may function differently during inflammatory responses.

The present invention relates to an antibody (anti-CCR1) or functional fragment thereof which binds mammalian CC-chemokine receptor 1 (CCR1, CKR-1) or a portion of CCR1. In one embodiment, the antibody has specificity for human CCR1 or portion thereof. In one embodiment, the antibody (immunoglobulin) is raised against an isolated and/or recombinant mammalian CCR1 or portion thereof (e.g., peptide) or against a host cell which expresses mammalian CCR1. In a preferred embodiment, the antibody specifically binds human CCR1 receptor or a portion thereof, and in a particularly preferred embodiment the antibody has specificity for a naturally occurring or endogenous human CCR1. Antibodies or functional fragments thereof which can inhibit one or more functions characteristic of a mammalian CCR1, such as a binding activity (e.g., ligand, inhibitor and/or promoter binding), a signaling activity (e.g., activation of a mammalian G protein, induction of a rapid and transient increase in the concentration of cytosolic free calcium $[Ca^{2+}]_i$), and/or stimulation of a cellular response (e.g., stimulation of chemotaxis, exocytosis or inflammatory mediator release by leukocytes, integrin activation) are also encompassed by the present invention, such as an antibody which can inhibit binding of a ligand (i.e., one or more ligands) to CCR1 and/or one or more functions mediated by CCR1 in response to a ligand. For example, in one aspect, the antibodies or functional fragments thereof can inhibit (reduce or prevent) the interaction of receptor with a natural ligand, such as MIP-1α, RANTES, MCP-2, MCP-3, leukotactin-1, HCC-1 or MPIF. In one embodiment, the ligand is MIP-1α, RANTES or HCC-1. In another aspect, an antibody or functional fragment thereof that binds to CCR1 can inhibit binding of MIP-1α, RANTES, MCP-2, MCP-3, leukotactin-1, HCC-1 or MPIF to mammalian CCR1 (e.g., human CCR1, non-human primate CCR1, murine CCR1). The antibodies or functional fragments thereof of the present invention can inhibit functions mediated by human CCR1, including leukocyte trafficking, T cell activation, inflammatory mediator release and/or leukocyte degranulation. In a particular embodiment, antibodies or functional fragments thereof demonstrate inhibition of chemokine-induced (e.g., MIP-1α, RANTES- or HCC-1-induced) chemotaxis of cells (e.g., CCR1-bearing cells), preferably at less than about 50 μg/ml, more preferably at less than about 20 μg/ml, and even more preferably at less than about 10 μg/ml.

In a further embodiment of the invention, the antibodies or functional fragments thereof of the invention can inhibit binding of a CCR1 ligand (e.g., a chemokine) to CCR1, preferably with an $IC_{50}$ of less than about 10 μg/ml, more preferably with an $IC_{50}$ of less than about 5 μg/ml, and even more preferably with an $IC_{50}$ of less than about 1.0 μg/ml. In another embodiment, the antibodies or functional fragments thereof of the invention can inhibit binding of MIP-1α to CCR1 with an $IC_{50}$ of about 0.5 μg/ml. In a further embodiment, the antibodies or fragments thereof of the invention can inhibit binding of RANTES to CCR1 with an $IC_{50}$ of about 0.7 μg/ml. In a further embodiment of the invention, the antibodies or fragments thereof bind CCR1 with an affinity of greater than about $5\times10^{-8}$ M, and preferably at least about $5\times10^{-9}$ M.

Figure 10A:
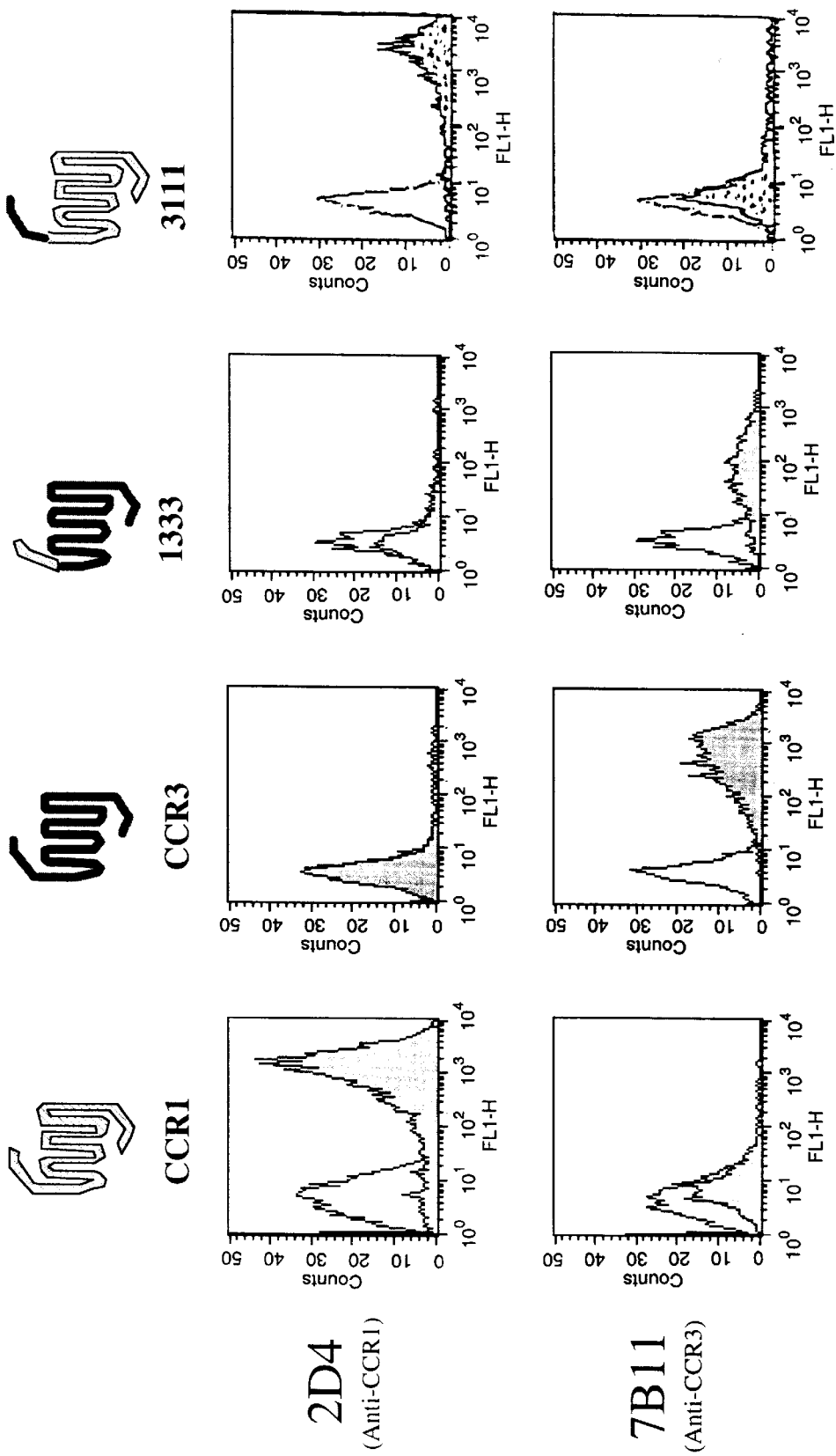
FIGS. 10A and 10B are schematic illustrations of the determination of the epitopic specificity of mAb 2D4 using CCR1/CCR3 receptor chimeras. The upper row of panels shows the binding of 2D4 (stippled outline) and a control antibody (open outline) to various receptor chimeras constructed from portions of CCR1 (stippled) and CCR3 (shaded) as indicated. The lower row of panels shows the binding of anti-CCR3 mAb 7B11 (stippled outline) and a control antibody (open outline) to the indicated receptor chimeras. mAb 2D4 binds to the second extracellular loop of CCR1.
Figure 10B:
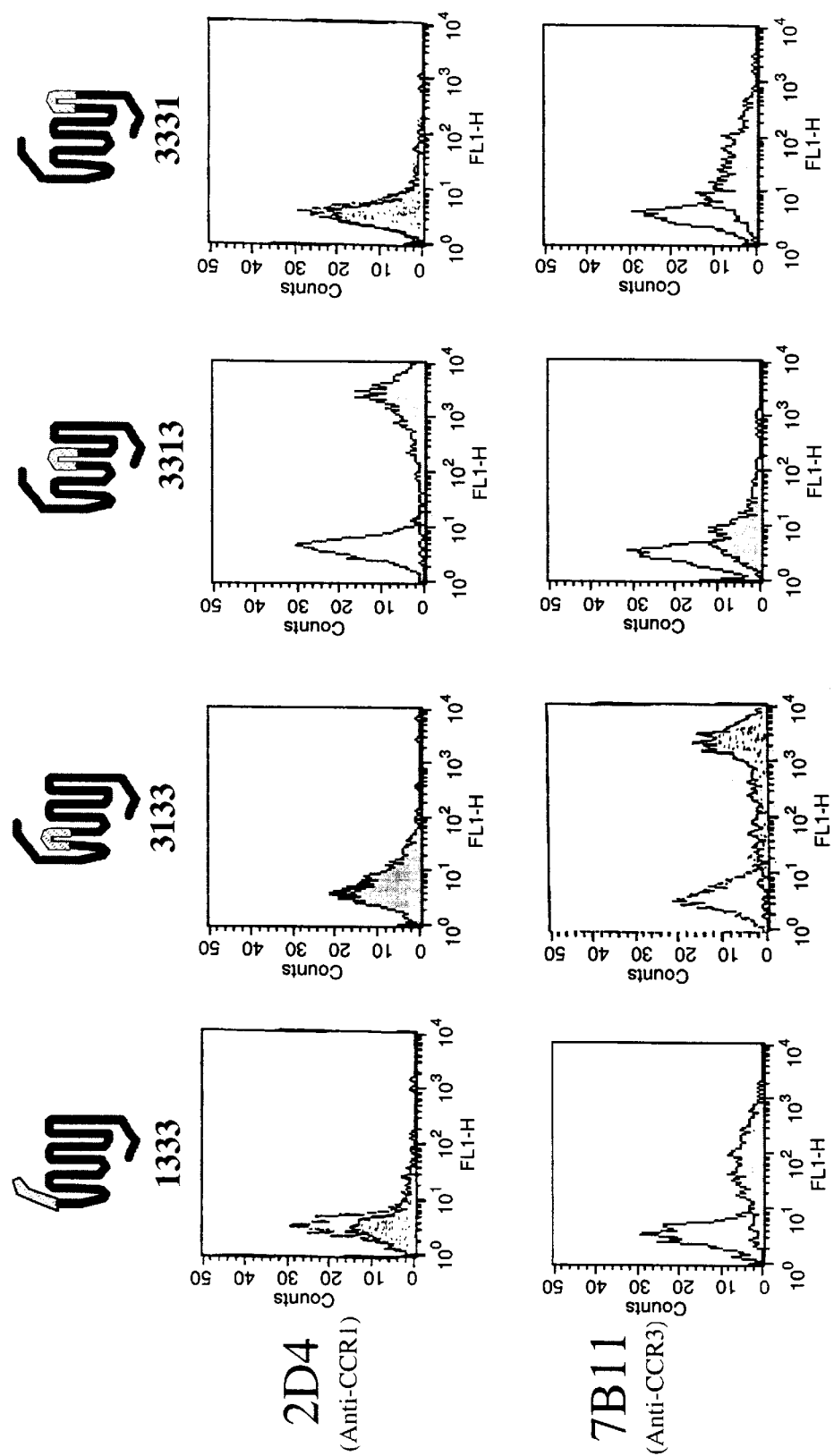

A murine monoclonal antibody specific for CCR1, designated 2D4, was produced as described herein. In a preferred embodiment, the antibodies of the present invention bind human CCR1, and have an epitopic specificity which is the same as or similar to that of murine 2D4 antibody described herein. Antibodies with an epitopic specificity which is the same as or similar to that of murine 2D4 monoclonal antibody can be identified using art-recognized techniques. For example, antibodies having an epitopic specificity which is the same as or similar to that of 2D4 can be identified by their ability to compete with murine 2D4 monoclonal antibody for binding to human CCR1 (e.g., to cells bearing human CCR1, such as transfectants bearing CCR1, CD8+ cells, CD4+ cells, CDR45RO+ cells, CD25+ cells, monocytes, dendiitic cells, macrophages and basophils), by their ability to inhibit binding of 2D4 to human CCR1, or through the use of receptor chimeras. Using receptor chimeras (Rucker et al., Cell 87:437–446 (1996)), mAb 2D4 has been shown to bind to the second extracellular loop of CCR1 (FIGS. 10A and 10B). For example, 2D4 can bind a region consisting essentially of amino acids 171 to 205 of human CCR1 (e.g., from about amino acid 171 to about amino acid 205; FIG. 12). Using these or other suitable techniques, antibodies having an epitopic specificity which is the same as or similar to that of an antibody of the present invention can be identified. The invention also relates to a bispecific antibody, or functional fragment thereof (e.g., F(ab')$_2$), which has the same or similar epitopic specificity as 2D4 and least one other antibody (see, e.g., U.S. Pat. No. 5,141,736 (Iwasa et al.), U.S. Pat. Nos. 4,444,878, 5,292,668, 5,523,210 (all to paulus el al.) and U.S. Pat. No. 5,496,549 (Yamazaki et al.).

A hybridoma cell line producing antibodies according to the present invention were deposited on Jan. 29, 1999, on behalf of LeukoSite, Inc., 215 First Street, ambridge, Mass. 02142, U.S.A., at the American Type Culture Collection, 10801 university Boulevard, Manassas, Va. 20110, U.S.A., under Accession No. HB-12644 (LS125-2D4-11-10-1 (2D4)). The present invention also pertains to the 2D4 hybridoma cell line deposited under ATCC Accession No. HB-12644, as well as to the monoclonal antibody produced by the 2D4 hybridoma cell line deposited under ATCC Accession No. HB-12644.

The antibodies of the present invention can be polyclonal or monoclonal, and the term "antibody" is intended to encompass both polyclonal and monoclonal antibodies. Furthermore, it is understood that methods described herein which utilize 2D4 can also utilize functional fragments (e.g., antigen-binding fragments) of 2D4, antibodies which have the same or similar epitopic specificity as 2D4, and combinations thereof, optionally in combination with antibodies or fragments having an epitopic specificity which is not the same as or similar to 2D4. Antibodies of the present invention can be raised against an appropriate immunogen, such as isolated and/or recombinant mammalian CCR1 protein or portion thereof, or synthetic molecules, such as synthetic peptides. In a preferred embodiment, cells which express receptor, such as transfected cells, can be used as immunogens or in a screen for antibody which binds receptor.

The antibodies of the present invention, and fragments thereof, are useful in therapeutic, diagnostic and research applications as described herein. The present invention encompasses an antibody or functional portion thereof of the present invention (e.g., mAb 2D4, or antigen-binding fragments thereof) for use in therapy (including prophylaxis) or diagnosis (e.g., of particular diseases or conditions as described herein), and use of such antibodies or functional portions thereof for the manufacture of a medicament for use in treatment of diseases or conditions as described herein.

Preparation of immunizing antigen, and polyclonal and monoclonal antibody production can be performed as described herein, or using other suitable techniques. A variety of methods have been described (see e.g., Kohler et al., *Nature*, 256: 495–497 (1975) and *Eur. J. immunol.* 6:511–519 (1976); Milstein et al., *Nature* 266: 550–552 (1977), Koprowski et al., U.S. Pat. No. 4,172,124; Harlow, E. and D. Lane, 1988, *Antibodies: A Laboratory Manual*, (Cold Spring Harbor Laboratory: Cold Spring Harbor, N.Y.); Current Protocols In Moleclular Biology, Vol. 2 (Supplement 27, Summer '94), Ausubel, F. M. et al., Eds., (John Wiley & Sons: New York, N.Y.), Chapter 11, (1991)). Generally, a hybridoma can be produced by fusing a suitable immortal cell line (e.g., a myeloma cell line such as SP2/0) with antibody producing cells. The antibody producing cell, preferably from the spleen or lymph nodes, are obtained from animals immunized with the antigen of interest. The fused cells (hybtidomas) can be isolated using selective culture conditions, and cloned by limiting dilution. Cells which produce antibodies with the desired binding properties can be selected by a suitable assay (e.g., ELISA).

Other suitable methods of producing or isolating antibodies which bind CCR1, including human or artificial antibodies, can be used, including, for example, methods which select recombinant antibody (e.g., single chain Fv or Fab) from a library, or which rely upon immunization of transgenic animals (e.g., mice) capable of producing a repertoire of human or artificial antibodies (see e.g., Jakobovits et al., *Proc. Ncatl. Acad. Sci. USA*, 90: 2551–2555 (1993); Jakobovits et al., *Nature*, 362: 255–258 (1993); Lonberg et al., U.S. Pat. No. 5,545,806; Surani et al., U.S. Pat. No. 5,545,807).

Single chain antibodies, and chimeric, humanized or primatized (CDR-grafted) antibodies, as well as chimeric or CDR-grafted single chain antibodies, and the like, comprising portions derived from different species, are also encompassed by the present invention and the term "antibody". The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. el al., WO 86/01533; Neuberger, M. S. et al., European Patent No. 0,194,276 B1; Winter, U.S. Pat. No. 5,225,539; Winter, European Patent No. 0,239,400 B1; and Queen et al., U.S. Pat. Nos. 5,585089, 5,698,761 and 5,698,762. See also, Newman, R. et al., *BioTechuology*, 10: 1455–1460 (1992), regarding puimatized antibody, and Ladner et al., U.S. Pat. No. 4,946,778 and Bird, R. E. et al., *Science*, 242: 423–426 (1988)) regarding single chain antibodies.

In addition, functional fragments of antibodies, including fragments of chimeric, humanized, primatized or single chain antibodies, can also be produced. Functional fragments of the foregoing antibodies retain at least one binding function and/or modulation function of the full-length antibody from which they are derived. Preferred functional fragments retain an antigen-binding function of a corresponding full-length antibody (e.g., retain the ability to bind a mammalian CCR1). Particularly preferred functional fragments retain the ability to inhibit one or more functions characteristic of a mammalian CCR1, such as a binding activity, a signaling activity, and/or stimulation of a cellular response. For example, in one embodiment, a functional fragment can inhibit the interaction of CCR1 with one or more of its ligands (e.g., MIP-1α, RANTES, MCP-2, MCP-3, leukotactin-1, HCC-1, or MPIF), and/or can inhibit one or more receptor-mediated functions, such as leukocyte trafficking, HIV entry into cells, T cell activation, inflammatory mediator release and/or leukocyte degranulation.

For example, antibody fragments capable of binding to a mammalian CCR1 receptor or portion thereof, including, but not limited to, Fv, Fab, Fab' and F(ab')$_2$ fragments are encompassed by the invention. Such fragments can be produced by enzymatic cleavage or by recombinant techniques, for example. For instance, papain or pepsin cleavage can generate Fab or F(ab')$_2$ fragments, respectively. Antibodies can also be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the CH$_1$ domain and hinge region of the heavy chain.

The temn "humanized immunoglobulin" as used herein refers to an immunoglobulin comprising portions of immunoglobulins of different origin, wherein at least one portion is of human origin. Accordingly, the present invention relates to a humanized immunoglobulin which binds mammalian CCR1 (e.g., human CCR1, murine CCR1), said immunoglobulin comprising an antigen-binding region of nonhuman origin (e.g., rodent) and at least a portion of an immunoglobulin of human origin (e.g., a human framework region, a human constant region or portion thereof). For example, the humanized antibody can comprise portions derived from an immunoglobulin of nonhuman origin with the requisite specificity, such as a mouse, and from immunoglobulin sequences of human origin (e.g., a chimeric immunoglobulin), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain). Another example of a humanized immunoglobulin of the present invention is an immunoglobulin containing one or more immunoglobulin chains comprising a CDR of nonhuman origin (e.g., one or more CDRs derived from an antibody of nonhuman origin) and a framework region derived from a light and/or heavy chain of human origin (e.g., CDR-grafted antibodies with or without framework changes). In one embodiment, the humanized immunoglobulin can compete with murine 2D4 monoclonal antibody for binding to human CCR1. In a preferred embodiment, the antigen-binding region of the humanized immunoglobulin (a) is derived from 2D4 monoclonal antibody (e.g., as in a humanized immunoglobulin comprising CDR1, CDR2 and CDR3 of the 2D4 light chain and CDR1, CDR2 and CDR3 of the 2D4 heavy chain). Chimeric or CDR-grafted single chain antibodies are also encompassed by the tern humanized immunoglobulin.

Such humanized immunoglobulins can be produced using synthetic and/or recombinant nucleic acids to prepare genes (e.g., CDNA) encoding the desired humanized chain. For example, nucleic acid (e.g., DNA) sequences coding for humanized variable regions can be constructed using PCR mutagenesis methods to alter DNA sequences encoding a human or humanized chain, such as a DNA template from a previously humanized variable region (see e.g., Kamman, M., et al., *Nucl. Acids Res.*, 17: 5404 (1989)); Sato, K., et al., *Cancer Research*, 53: 851–856 (1993); Daugherty, B. L. et al., *Nucleic Acids Res.*, 19(9): 2471–2476 (1991); and Lewis, A. P. and J. S. Crowe, *Gene*, 101: 297–302 (1991)). Using these or other suitable methods, variants can also be readily produced. In one embodiment, cloned variable regions can be mutagenized, and sequences encoding variants with the desired specificity can be selected (e.g., from a phage library; see e.g., Krebber et at., U.S. Pat. No. 5,514,548; Hoogenboom et al., WO 93/06213, published Apr. 1, 1993; Knappik et al., WO 97/08320, published Mar. 6, 1997)).

Anti-idiotypic antibodies are also provided. Anti-idiotypic antibodies recognize antigenic detenninants associated with the antigen-binding site of another antibody. Anti-idiotypic antibodies can be prepared against second antibody by immunizing an animal of the same species, and preferably of the same strain, as the animal used to produce the second antibody. See e.g., U.S. Pat. No. 4,699,880.

The present invention also pertains to the 2D4 hybridoma cell line deposited under ATCC Accession No. HB-12644, as well as to the monoclonal antibody produced by the 2D4 hybridoma cell line deposited under ATCC Accession No. HB-12644 and antigen-binding fragments thereof. The cell lines of the present invention have uses other than for the production of the monoclonal antibodies. For example, the cell lines of the present invention can be fused with other cells (such as suitably drug-marked human myeloma, mouse myeloma, human-mouse heteromyeloma or human lymphoblastoid cells) to produce additional hybridomas, and thus provide for the transfer of the genes encoding the monoclonal antibodies. In addition, the cell lines can be used as a source of nucleic acids encoding the anti-CCR1 immunoglobulin chains, which can be isolated and expressed (e.g., upon transfer to other cells using any suitable technique (see e.g., Cabilly et al., U.S. Pat. No. 4,816,567; Winter, U.S. Pat. No. 5,225,539)). For instance, clones comprising a rearranged anti-CCR1 liglht or heavy chain can be isolated (e.g., by PCR) or CDNA libraries can be prepared from mRNA isolated from the cell lines, and cDNA clones encoding an anti-CCR1 immunoglobulini chain can be isolated. Thus, nucleic acids encoding the heavy and/or light chains of the antibodies or portions thereof can be obtained and used in accordance with recombinant DNA techniques for the production of the specific immunoglobulin, immunoglobulin chain, or variants thereof (e.g., humanized immunoglobulins) in a variety of host cells or in an in vitro translation system. For example, the nucleic acids, including cDNAs, or derivatives thereof encoding variants such as a humanized immunoglobulin or immutoglobulin chain, can be placed into suitable prokaryotic or eukaryotic vectors (e.g., expression vectors) and introduced into a suitable host cell by an appropriate method (e.g., transformation, transfection, electroporation, infection), such that the nucleic acid is operably linked to one or more expression control elements (e.g., in the vector or integrated into the host cell genomc). For production, host cells can be maintained under conditions suitable for expression (e.g., in the presence of inducer, suitable media supplemented with appropriate salts, growth factors, antibiotic, nutritional supplements, etc.), whereby the encoded polypeptide is produced. If desired, the encoded protein can be recovered and/or isolated (e.g., from the host cells, medium, milk). It will be appreciated that the method of production encompasses expression in a host cell of a transgenic animal (see e.g., WO 92/03918, GenPharm International, published Mar. 19, 1992).

As described herein, antibodies and functional fragments thereof of the present invention can block (inhibit) binding of a ligand to CCR1 and/or inhibit one or more functions associated with binding of the ligand to the CCR1. As discussed below various methods can be used to assess inhibition of binding of a ligand to CCR1 and/or function associated with binding of the ligand to the receptor.

Binding Assays

As used herein "mammalian CCR1" refers to naturally occurring or endogenous mammalian CCR1 proteins and to proteins having an amino acid sequence which is the same as that of a naturally occurring or endogenous corresponding mammalian CCR1 protein (e.g., recombinant proteins). Accordingly, as defined herein, the term includes mature receptor protein, polymorphic or allelic variants, and other isoforms of a mammalian CCR1 (e.g., produced by alternative splicing or other cellular processes), and modified or unmodified forms of the foregoing (e.g., glycosylated, unlycosylated). Mammalian CCR1 proteins can be isolated and/or recombinant proteins (including synthetically produced proteins). Naturally occurring or endogenous mammalian CCR1 proteins include wild type proteins such as mature CCR1, polymorphic or allelic variants and other isoforms which occur naturally in mammals (e.g., humans, non-human primates). Such proteins can be recovered or isolated from a source which naturally produces mammalian CCR1, for example. These proteins and mammalian CCR1 proteins having the same amino acid sequence as a naturally occurring or endogenous corresponding mammalian CCR1, are referred to by the name of the corresponding mammal. For example, where the corresponding mammal is a human, the protein is designated as a human CCR1 protein (e.g., a recombinant human CCR1 produced in a suitable host cell).

"Functional variants" of mammalian CCR1 proteins include functional fragments, functional mutant proteins, and/or functional fusion proteins (e.g., produced via mutagenesis and/or recombinant techniques). Generally, fragments or portions of mammalian CCR1 proteins include those having a deletion (i.e., one or more deletions) of an amino acid (i.e., one or more amino acids) relative to the mature mammalian CCR1 protein (such as N-terminal, C-tenninal or internal deletions). Fragments or portions in which only contiguous amino acids have been deleted or in which non-contiguous amino acids have been deleted relative to mature mammalian CCR1 protein are also envisioned.

Generally, mutants of mammalian CCR1 proteins include natural or artificial variants of a mammalian CCR1 protein differing by the addition, deletion and/or substitution of one or more contiguous or non-contiguous amino acid residues (e.g., receptor chimeras). Such mutations can be in a conserved region or nonconserved region (compared to other CXC ($\alpha$) and/or CC ($\beta$) chemokine receptors), extracellular, cytoplasmic, or transmembrane region, for example.

Generally, fusion proteins encompass polypeptides comprising a mammalian CCR1 (e.g., human CCR1) or a variant thereof as a first moiety, linked via a peptide bond to a second moiety not occurring in the mammalian CCR1 as found in nature. Thus, the second moiety can be an amino acid, oligopeptide or polypeptide. The first moiety can be in an N-terminal location, C-terminal location or internal to the fusion protein. In one embodiment, the fusion protein comprises an affinity ligand (e.g., an enzyme, an antigen, epitope tag) as the first moiety, and a second moiety comprising a linker sequence and human CCR1 or a portion thereof. Additional (e.g., third, fourth) moieties can be present as appropriate.

A "functional fragment or portion", "functional mutant" and/or "functional fusion protein" of a mammalian CCR1 protein refers to an isolated and/or recombinant protein or polypeptide which has at least one function characteristic of a mammalian CCR1 protein as described herein, such as a binding activity, a signaling activity and/or ability to stimulate a cellular response. Preferred functional variants can bind a ligand (i.e., one or more ligands such as MIP-1$\alpha$, RANTES, MCP-2, MCP-3, leukotactin-1, HCC-1, or MPIF), and are referred to herein as "ligand binding variants".

In one embodiment, a functional variant of mammalian CCR1 shares at least about 85% sequence identity with said mammalian CCR1, preferably at least about 90% sequence identity, and more preferably at least about 95% sequence identity with said mammalian CCR1. In another embodiment, a functional fusion protein comprises a first moiety which shares at least about 85% sequence identity with a mammalian CCR1, preferably at least about 90% sequence identity, and more preferably at least about 95% sequence identity with a mammalian CCR1. Sequence identity can be determined using a suitable program, such as the Blastx program (Version 1.4), using appropriate parameters, such as default parameters. In one embodiment, parameters for Blastx search are scoring matrix BLOSUM62, W=3. In another embodiment, a functional variant comprises a nucleic acid sequence which is different from the naturally-occurring nucleic acid molecule but which, due to the degeneracy of the genetic code, encodes mammalian CCR1 or a portion thereof.

A composition comprising an isolated and/or recombinant mammalian CCR1 or functional variant thereof can be maintained under conditions suitable for binding, the mammalian CCR1 or variant is contacted with an antibody or fragment to be tested, and binding is detected or measured directly or indirectly. In one embodiment, cells which naturally express CCR1 or cells comprising a recombinant nucleic acid sequence which encodes a mammalian CCR1 or variant thereof are used. The cells are maintained under conditions appropriate for expression of receptor. The cells are contacted with an antibody or fragment under conditions suitable for binding (e.g., in a suitable binding buffer), and binding is detected by standard techniques. To determine binding, the extent of binding can be determined relative to a suitable control (e.g., compared with background determined in the absence of antibody, compared with binding of a second antibody (i.e., a standard), compared with binding of antibody to untransfected cells). A cellular fraction, such as a membrane fraction, containing receptor or liposomes comprising receptor can be used in lieu of whole cells.

In one embodiment, the antibody is labeled with a suitable label (e.g., fluorescent label, isotope label, antigen or epitope label, enzyme label), and binding is determined by detection of the label. In another embodiment, bound antibody can be detected by labeled second antibody. Specificity of binding can be assessed by competition or displacement, for example, using unlabeled antibody or a ligand as competitor.

Binding inhibition assays can also be used to identify antibodies or fragments thereof which bind CCR1 and inhibit binding of another compound such as a ligand (e.g., MIP-1α, RANTES, MCP-2, MCP-3, leukotactin-1, HCC-1, or MPIF) to CCR1 or a functional variant. For example, a binding assay can be conducted in which a reduction in the binding of a ligand of CCR1 (in the presence of an antibody such as 2D4), as compared to binding of the ligand in the absence of the antibody, is detected or measured. A composition comprising an isolated and/or recombinant mammalian CCR1 or functional variant thereof can be contacted with the ligand and antibody simultaneously, or one after the other, in either order. A reduction in the extent of binding of the ligand in the presence of the antibody, is indicative of inhibition of binding by the antibody. For example, binding of the ligand could be decreased or abolished.

In one embodiment, direct inhibition of the binding of a ligand (e.g., a chemokine such as MIP-1 α, RANTES, MCP-2, MCP-3, leukotactin-1, HCC-1, or MPIF) to a mammalian CCR1 or variant thereof by an antibody or fragment is monitored. For example, the ability of an antibody to inhibit the binding of $^{125}$I-labeled MIP-1α, $^{125}$I-labeled RANTES, $^{125}$I-labeled MCP-2, $^{125}$I-labeled MCP-3, $^{125}$I-labeled leukotactin-1, $^{125}$I-labeled HCC-1 or 125I-labeled MPIF to mammalian CCR1 can be monitored. Such an assay can be conducted using suitable cells bearing CCR1 or a functional variant thereof, such as isolated blood cells (e.g., T cells) or a suitable cell line naturally expressing CCR1, or a cell line containing nucleic acid encoding a mammalian CCR1, or a membrane fraction from said cells, for instance.

Other methods of identifying the presence of an antibody which binds CCR1 are available, such as other suitable binding assays, or methods which monitor events which are triggered by receptor binding, including signaling function and/or stimulation of a cellular response (e.g., leukocyte trafficking).

It will be understood that the inhibitory effect of antibodies of the present invention can be assessed in a binding inhibition assay. Competition between antibodies for receptor binding can also be assessed in the method. Antibodies which are identified in this manner can be further assessed to determine whether, subsequent to binding, they act to inhibit other functions of CCR1 and/or to assess their therapeutic utility.

Signaling Assays

The binding of a ligand or promoter, such as an agonist, to CCR1 can result in signaling by this G protein-coupled receptor, and the activity of G proteins as well as other intracellular signaling molecules is stimulated. The induction of signaling function by a compound (e.g., an antibody or fragment thereof can be monitored using any suitable method. Such an assay can be used to identify antibody agonists of CCR1. The inhibitory activity of an antibody or functional fragment thereof can be determined using a ligand or promoter in the assay, and assessing the ability of the antibody to inhibit the activity induced by ligand or promoter.

G protein activity, such as hydrolysis of GTP to GDP, or later signaling events triggered by receptor binding, such as induction of rapid and transient increase in the concentration of intracellular (cytosolic) free calcium $[Ca^{2+}]_i$, can be assayed by methods known in the art or other suitable methods (see e.g., Neote, K. et al., *Cell*, 72: 415–425 1993); Van Riper et al., *J. Exp. Med.*, 177: 851–856 (1993); Dahinden, C. A. et al, *J. Exp. Med.*, 179: 751–756 (1994)).

For example, the functional assay of Sledziewski et al. using hybrid G protein coupled receptors can be used to monitor the ability a ligand or promoter to bind receptor and activate a G protein (Sledziewski et al., U.S. Pat. No. 5,284,746, the teachings of which are incorporated herein by reference).

Such assays can be performed in the presence of the antibody or fragment thereof to be assessed, and the ability of the antibody or fragment to inhibit the activity induced by the ligand or promoter is determined using known methods and/or methods described herein.

Chemotaxis and Assays of Cellular Stimulation

Chemotaxis assays can also be used to assess the ability of an antibody or functional fragment thereof to block binding of a ligand to mammalian CCR1 or functional variant thereof and/or inhibit fuinction associated with binding of the ligand to the receptor. These assays are based on the functional migration of cells in vitro or in vivo induced by a compound. Chemotaxis can be assessed as described in the Examples, e.g., in an assay utilizing a 96-well chemotaxis plate, or using other art-recognized methods for assessing chemotaxis. For example, the use of an in vitro transendothelial chemotaxis assay is described by Springer et al. (Springer et al., WO 94/20142, published Sep. 15, 1994, the teachings of which are incorporated herein by reference; see also Berman et al., *Immunol. Invest.* 17: 625–677 (1988)). Migration across endothelium into collagen gels has also been described (Kavanaugh et al., *J. Inimutiol.*, 146: 4149–4156 (1991)). Stable transfectants of mouse L1.2 pre-B cells or of other suitable host cells capable of chemotaxis can be used in chemotaxis assays, for example.

Generally, chemotaxis assays monitor the directional movement or migration of a suitable cell (such as a leukocyte (e.g., lymphocyte, eosinophil, basophil)) into or through a barrier (e.g., endothelium, a filter), toward increased levels of a compound, from a first surface of the barrier toward an opposite second surface. Membranes or filters provide convenient barriers, such that the directional movement or migration of a suitable cell into or through a filter, toward increased levels of a compound, from a first surface of the filter toward an opposite second surface of the filter, is monitored. In some assays, the membrane is coated with a substance to facilitate adhesion, such as ICAM-1, fibronectin or collagen. Such assays provide an in vitro approximation of leukocyte "homing".

For example, one can detect or measure inhibition of the migration of cells in a suitable container (a containing means), from a first chamber into or through a microporous membrane into a second chamber which contains an antibody to be tested, and which is divided from the first chamber by the membrane. A suitable membrane, having a suitable pore size for monitoring specific migration in response to compound, including, for example, nitrocellulose, polycarbonate, is selected. For example, pore sizes of about 3–8 microns, and preferably about 5–8 microns can be used. Pore size can be uniform on a filter or within a range of suitable pore sizes.

To assess migration and inhibition of migration, the distance of migration into the filter, the number of cells crossing the filter that remain adherent to the second surface of the filter, and/or the number of cells that accumulate in the second chamber can be determined using standard techniques (e.g., microscopy). In one embodiment, the cells are labeled with a detectable label (e.g., radioisotope, fluorescent label, antigen or epitope label), and migration can be assessed in the presence and absence of the antibody or fragment by determining the presence of the label adherent to the membrane and/or present in the second chamber using an appropriate method (e.g., by detecting radioactivity, fluorescence, immunoassay). The extent of migration induced by an antibody agonist can be determined relative to a suitable control (e.g., compared to background migration determined in the absence of the antibody, compared to the extent of migration induced by a second compound (i.e., a standard), compared with migration of untransfected cells induced by the antibody).

In one embodiment, particularly for T cells, monocytes or cells expressing a mammalian CCR1, transendothelial migration can be monitored. In this embodiment, transmigration through an endothelial cell layer is assessed. To prepare the cell layer, endothelial cells can be cultured on a microporous filter or membrane, optionally coated with a substance such as collagen, fibronectin, or other extracellular matrix proteins, to facilitate the attachment of endothelial cells. Preferably, endothelial cells are cultured until a confluent monolayer is formed. A variety of mammalian endothelial cells can are available for monolayer formation, including for example, vein, artery or microvascular endothelium, such as human umbilical vein endothelial cells (Clonetics Corp, San Diego, Calif.). To assay chemotaxis in response to a particular mammalian receptor, endothelial cells of the same mammal are preferred; however endothelial cells from a heterologous mammalian species or genus can also be used.

Generally, the assay is performed by detecting the directional migration of cells into or through a membrane or filter, in a direction toward increased levels of a compound, from a first surface of the filter toward an opposite second surface of the filter, wherein the filter contains an endothelial cell layer on a first surface. Directional migration occurs from the area adjacent to the first surface, into or through the membrane, towards a compound situated on the opposite side of the filter. The concentration of compound present in the area adjacent to the second surface, is greater than that in the area adjacent to the first surface.

In one embodiment used to test for an antibody inhibitor, a composition comprising cells capable of migration and expressing a mammalian CCR1 receptor can be placed in the first chamber. A composition comprising one or more ligands or promoters capable of inducing chemotaxis of the cells in the first chamber (having chemoattractant function) is placed in the second chamber. Preferably shortly before the cells are placed in the first chamber, or simultaneously with the cells, a composition comprising the antibody to be tested is placed, preferably, in the first chamber. Antibodies or functional fragments thereof which can bind receptor and inhibit the induction of chemotaxis, by a ligand or promoter, of the cells expressing a mammalian CCR1 in this assay are inhibitors of receptor function (e.g., inhibitors of stimulatory function). A reduction in the extent of migration induced by the ligand or promoter in the presence of the antibody or fragment is indicative of inhibitory activity. Separate binding studies (see above) could be performed to determine whether inhibition is a result of binding of the antibody to receptor or occurs via a different mechanism.

In vivo assays which monitor leukocyte infiltration of a tissue, in response to injection of a compound (e.g., chemokine or antibody) in the tissue, are described below (see Models of Inflammation). These models of iil vivo homing measure the ability of cells to respond to a ligand or promoter by emigration and chemotaxis to a site of inflammation and to assess the ability of an antibody or fragment thereof to block this emigration.

In addition to the methods described, the effects of an antibody or fragment on the stimulatory function of CCR1 can be assessed by monitoring cellular responses induced by active receptor, using suitable host cells containing receptor.

Identification of Additional Ligands, Inhibitors and/or Promoters of Mammalian CCR1 Function The assays described above, which can be used to assess binding and function of the antibodies and fragments of the present invention, can be adapted to identify additional ligands or other substances which bind a mammalian CCR1 or functional variant thereof, as well as inhibitors and/or promoters of mammalian CCR1 function. For example, agents having the same or a similar binding specificity as that of an antibody of the present invention or functional portion thereof can be identified by a competition assay with said antibody or portion thereof. Thus, the present invention also encompasses methods of identifying ligands of the receptor or other substances which bind a mammalian CCR1 protein, as well as inhibitors (e.g., antagonists) or promoters (e.g., agonists) of receptor function. In one embodiment, cells beaiing a mammalian CCR1 protein or functional variant thereof (e.g., leukocytes, cell lines or suitable host cells which have been engineered to express a mammalian CCR1 protein or functional variant encoded by a nucleic acid introduced into said cells) are used in an assay to identify and assess the efficacy of ligands or other substances which bind receptor, including inhibitors or promoters of receptor function. Such cells are also useful in assessing the function of the expressed receptor protein or polypeptide.

According to the present invention, ligands and other substances which bind receptor, inhibitors and promoters of receptor function can be identified in a suitable assay, and further assessed for therapeutic effect. Inhibitors of receptor function can be used to inhibit (reduce or prevent) receptor activity, and ligands and/or promoters can be used to induce (trigger or enhance) normal receptor function where indicated. These inhibitors can be used in methods of treating inflammatory diseases, including autoimmune disease and graft rejection, comprising administering an inhibitor of receptor function to an individual (e.g., a mammal). Ligands and/or promoters identified as described herein can be used in a method of stimulating receptor function by administering a novel ligand or promoter of receptor function to an individual, providing a new approach to selective stimulation of leukocyte function, which is useful, for example, in the treatment of infectious diseases and cancer.

As used herein, a "ligand" of a mammalian CCR1 protein refers to a particular class of substances which bind to a mammalian CCR1 protein, including natural ligands and synthetic and/or recombinant forms of natural ligands. Infectious agents having a tropism for mammalian CCR1-positive cells (e.g., viruses such as HIV) can also bind to a mammalian CCR1 protein. A natural ligand of a selected mammalian receptor is of a mammalian origin which is the same as that of the mammalian CCR1 protein (e.g., a chemokine such as MIP-1α, RANTES, MCP-2, MCP-3, leukotactin- 1, HCC-1, and/or MPIF). In a preferred embodiment, ligand binding of a mammalian CCR1 protein occurs with high affinity.

As used herein, an "inhibitor" is a substance which inhibits (decreases or prevents) at least one function characteristic of a mammalian CCR1 protein (e.g., a human CCR1), such as a binding activity (e.g., ligand binding, promoter binding, antibody binding), a signaling activity (e.g., activation of a mammalian G protein, induction of rapid and transient increase in the concentration of cytosolic free calcium $[Ca^{2+}]_i$), and/or cellular response function (e.g., stimulation of chemotaxis, exocytosis or inflammatory mediator release by leukocytes). An inhibitor is also a substance which inhibits HIV entry into a cell. The term inhibitor refers to substances including antagonists which bind receptor (e.g., an antibody, a mutant of a natural ligand, small molecular weight organic molecules, other competitive inhibitors of ligand binding), and substances which inhibit receptor function without binding thereto (e.g., an anti-idiotypic antibody).

As used herein, a "promoter" is a substance which promotes (induces, causes, enhances or increases) at least one function characteristic of a mammalian CCR1 protein (e.g., a human CCR1), such as a binding activity (e.g., ligand, inhibitor and/or promoter binding), a signaling activity (e.g., activation of a mammalian G protein, induction of rapid and transient increase in the concentration of cytosolic free calcium $[Ca^{2+}]_i$), and/or a cellular response function (e.g., stimulation of chemotaxis, exocytosis or inflammatory mediator release by leukocytes). The term promoter refers to substances including agonists which bind receptor (e.g., an antibody, a homolog of a natural ligand from another species), and substances which promote receptor function without binding thereto (e.g., by activating an associated protein). In a preferred embodiment, the agonist is other than a homolog of a natural ligand.

Thus, the invention also relates to a method of detecting or identifying an agent which binds a mammalian CC-chemokine receptor 1 or ligand binding variant thereof, including ligands, inhibitors, promoters, and other substances which bind a mammalian CCR1 receptor or functional variant. According to the method, an agent to be tested, an antibody or antigen-binding fragment of the present invention (e.g., 2D4, an antibody having an epitopic specificity which is the same as or similar to that of 2D4, and antigen-binding fragments thereof) and a composition comprising a mammalian CC-chemokine receptor 1 or a ligand binding variant thereof can be combined. The foregoing components are combined under conditions suitable for binding of the antibody or antigen-binding fragment to mammalian CC-chemokine receptor 1 or a ligand binding variant thereof, and binding of the antibody or fragment to the mammalian CC-chemokine receptor 1 or ligand binding variant is detected or measured, either directly or indirectly, according to methods described herein or other suitable methods. A decrease in the amount of complex formed relative to a suitable control (e.g., in the absence of the agent to be tested) is indicative that the agent binds said receptor or variant. The composition comprising a mammalian CC-chemokine receptor 1 or a ligand binding variant thereof can be a membrane fraction of a cell bearing recombinant chemokine receptor 1 protein or ligand binding variant thereof. The antibody or fragment thereof can be labeled with a label such as a radioisotope, spin label, antigen or epitope label, enzyme label, fluorescent group and chemiluminescent group.

In one embodiment, the invention relates to a method of detecting or identifying an agent which binds a mammalian CC-chemokine receptor 1 or a ligand binding variant thereof, comprising combining an agent to be tested, an antibody or antigen-binding fragment of the present invention (e.g., 2D4, an antibody having an epitopic specificity which is the same as or similar to that of 2D4, or antigen-binding fragments thereof) and a cell bearing a mammalian CC-chemokine receptor 1 or a ligand binding variant thereof. The foregoing components are combined under conditions suitable for binding of the antibody or antigen-binding fragment to the CCR1 protein or ligand binding variant thereof, and binding of the antibody or fragment to the mammalian CC-chemokine receptor 1 or variant is detected or measured, either directly or indirectly, by methods described herein and or other suitable methods. A decrease in the amount of complex formed relative to a suitable control is indicative that the agent binds the receptor or variant. The antibody or fragment thereof can be labeled with a label selected from the group consisting of a radioisotope, spin label, antigen or epitope label, enzyme label, fluorescent group and chemiluminescent group. These and similar assays can be used to detect agents, including ligands (e.g., chemokines or strains of HIV which interact with CCR1) or other substances, including inhibitors or promoters of receptor function, which can bind CCR1 and compete with the antibodies described herein for binding to the receptor.

The assays described above can be used, alone or in combination with each other or other suitable methods, to identify ligands or other substances which bind a mammalian CCR1 protein, and inhibitors or promoters of a mammalian CCR1 protein or variant. The ini vitro methods of the present invention can be adapted for high-throughput screening in which large numbers of samples are processed (e.g., a 96-well format). Cells expressing mammalian CCR1 (e.g., human CCR1) at levels suitable for high-throughput screening can be used, and thus, are particularly valuable in the identification and/or isolation of ligands or other substances which bind receptor, and inhibitors or promoters of mammalian CCR1 proteins. Expression of receptor can be monitored in a variety of ways. For instance, expression can be monitored using antibodies of the present invention which bind receptor or a portion thereof. Also, commercially available antibodies can be used to detect expression of an antigen- or epitope-tagged fusion protein comprising a receptor protein or polypeptide (e.g., FLAG tagged receptors), and cells expressing the desired level can be selected.

Nucleic acid encoding a mammalian CCR1 protein or functional variant thereof can be incorporated into an expression system to produce a receptor protein or polypeptide. An isolated and/or recombinant mammalian CCR1 protein or variant, such as a receptor expressed in cells stably or transiently transfected with a construct comprisinig a recombinant nucleic acid encoding a mammalian CCR1 protein or variant, or in a cell fraction containing receptor (e.g., a membrane fraction from transfected cells, liposomes incorporating receptor), can be used in tests for receptor function. The receptor can be further purified if desired. Testing of receptor function can be carried out iil vitro or in vivo.

An isolated and/or recombinant mammalian CCR1 protein or functional variant thereof, such as a human CCR1, can be used in the present method, in which the effect of a compound is assessed by monitoring receptor function as described herein or using other suitable techniques. For example, stable or transient transfectants (e.g., baculovirus infected Sf9 cells, stable tranfectants of mouse L1.2 pre-B cells), can be used in binding assays. Stable transfectants of Jurkat cells or of other suitable cells capable of chemotaxis can be used (e.g., mouse L1.2 pre-B cells) in chemotaxis assays, for example.

According to the method of the present invention, compounds can be individually screened or one or more compounds can be tested simultaneously according to the methods herein. Where a mixture of compounds is tested, the compounds selected by the processes described can be separated (as appropriate) and identified by suitable methods (e.g., PCR, sequencing, chromatography, mass spectroscopy). The presence of one or more compounds (e.g., a ligand, inhibitor, promoter) in a test sample can also be determined according to these methods.

Large combinatorial libraries of compounds (e.g., organic compounds, recombinant or synthetic peptides, "peptoids", nucleic acids) produced by combinatorial chemical synthesis or other methods can be tested (see e.g., Zuckerman, R. N. et al., *J Med. Chem.*, 37: 2678–2685 (1994) and references cited therein; see also, Ohlmeyer, M. H. J. et al., *Proc. Natl. Acad. Sci. USA* 90:10922–10926 (1993) and DeWitt, S. H. et al., *Proc. Natl. Acacl. Sci. USA* 90:6909–6913 (1993), relating to tagged compounds; Rutter, W. J. et al. U.S. Pat. No. 5,010,175; Huebner, V. D. et al., U.S. Pat. No. 5,182,366; and Geysen, H. M., U.S. Pat. No. 4,833,092). Where compounds selected from a combinatorial library by the present method canry unique tags, identification of individual compounds by chromatographic methods is possible.

In one embodiment, phage display methodology is used. For example, a mammalian CCR1 protein or functional valiant, an antibody or functional portion thereof of the present invention, and a phage (e.g., a phage or collection of phage such as a library) displaying a polypeptide, can be combined under conditions appropriate for binding of the antibody or portion thereof to the mammalian CCR1 protein or variant (e.g., in a suitable binding buffer). Phage which can compete with the antibody or portion thereof and bind to the mammalian CCR1 protein or variant can be detected or selected using standard techniques or other suitable methods. Bound phage can be separated from receptor using a suitable elution buffer. For example, a change in the ionic strength or pH can lead to a release of phage. Alternatively, the elution buffer can comprise a release component or components designed to disrupt binding of compounds (e.g., one or more compounds which can disrupt binding of the displayed peptide to the receptor, such as a ligand, inhibitor, and/or promoter which competitively inhibits binding). Optionally, the selection process can be repeated or another selection step can be used to further enrich for phage which bind receptor. The displayed polypeptide can be characterized (e.g., by sequencing phage DNA). The polypeptides identified can be produced and further tested for binding, and for inhibitor or promoter function. Analogs of such peptides can be produced which will have increased stability or other desirable properties.

In one embodiment, phage expressing and displaying fusion proteins comprising a coat protein with an N-teninal peptide encoded by random sequence nucleic acids can be produced. Suitable host cells expressing a mammalian CCR1 protein or variant and an anti-CCR1 antibody or functional portion thereof, are combined with the phage, bound phage are selected, recovered and characterized. (See e.g., Doorbar and Winter, *J. Mol. Biol.* 244:361 (1994), discussing a phage display procedure used with a G protein-coupled receptor, and WO 97/08320 (Morphosys), published Mar. 6, 1997).

Other sources of potential ligands or other substances which bind to, or inhibitors and/or promoters of, mammalian CCR1 proteins include, but are not limited to, variants of CCR1 ligands, including naturally occurring, synthetic or recombinant variants of MIP-1α, RANTES, MCP-2, MCP-3, leukotactin-1, HCC-1, or MPIF, substances such as other chemoattractants or chemokines, variants thereof, low molecular weight organic molecules, other inhibitors and/or promoters (e.g., anti-CCR1 antibodies, antagonists, agonists), other G protein-coupled receptor ligands, inhibitors and/or promoters (e.g., antagonists or agonists), and soluble portions of a mammalian CCR1 receptor, such as a suitable receptor peptide or analog which can inhibit receptor function (see e.g., Murphy, R. B., WO 94/05695).

Models of Inflammation

In vivo models of inflammation are available which can be used to assess the effects of antibodies and fragments of the invention in vivo as therapeutic agents. For example, leukocyte infiltration upon intradermal injection of a chemokine and an antibody or fragment thereof reactive with mammalian CCR1 into a suitable animal, such as rabbit, mouse, rat, guinea pig or rhesus macaque can be monitored (see e.g., Van Damme, J. et al.,*J. Exp. Med.*, 176: 59–65 (1992); Zachariae, C. O. C. et al., *J. Exp. Med.* 171: 2177–2182 (1990); Jose, P. J. et al., *J. Exp. Med.* 179: 881–887 (1994)). In one embodiment, skin biopsies are assessed histologically for infiltration of leukocytes (e.g., eosinophils, granulocytes). In another embodiment, labeled cells (e.g., stably transfected cells expressing a mammalian CCR1, labeled with $^{111}$In for example) capable of chemotaxis and extravasation are administered to the animal. For example, an antibody or fragment to be assessed can be administered, either before, simultaneously with or after ligand or agonist is administered to the test animal. A decrease of the extent of infiltration in the presence of antibody as compared with the extent of infiltration in the absence of inhibitor is indicative of inhibition.

Diagnostic and Therapeutic Applications

The antibodies and fragments of the present invention are useful in a variety of applications, including research, diagnostic and therapeutic applications. In one embodiment, the antibodies are labeled with a suitable label (e.g., fluorescent label, chemiluminescent label, isotope label, antigen or epitope label or enzyme label). For instance, they can be used to isolate and/or purify receptor or portions thereof, and to study receptor structure (e.g., conformation) and function.

In addition, the various antibodies of the present invention can be used to detect CCR1 or to measure the expression of receptor, for example, on T cells (e.g., CD26+ cells, CD45RO+ cells), neutrophils, eosinophils, and/or on cells transfected with a receptor gene. Thus, they also have utility in applications such as cell sorting (e.g., flow cytometry, fluorescence activated cell sorting), for diagnostic or research purposes.

The anti-CCR1 antibodies of the present invention have value in diagnostic applications. An anti-CCR1 antibody or fragment thereof can be used to monitor expression of this receptor in individuals, similar to the way anti-CD4 has been used as a diagnostic indicator of HIV stage.

Typically, diagnostic assays entail detecting the formation of a complex resulting from the binding of an antibody or fragment thereof to CCR1. For diagnostic purposes, the antibodies or antigen-binding fragments can be labeled or unlabeled. The antibodies or fragments can be directly labeled. A variety of labels can be employed, including, but not limited to, radionuclides, fluorescers, enzymes, enzyme substrates, enzyme cofactors, enzyme inhibitors and ligands (e.g., biotin, haptens). Numerous appropriate immunoassays are known to the skilled artisan (see, for example, U.S. Pat. Nos. 3,817,827; 3,850,752; 3,901,654 and 4,098,876). When unlabeled, the antibodies or fragments can be detected using suitable means, as in agglutination assays, for example. Unlabeled antibodies or fragments can also be used in combination with another (i.e., one or more) suitable reagent which can be used to detect antibody, such as a labeled antibody (e.g., a second antibody) reactive with the first antibody (e.g., anti-idiotype antibodies or other antibodies that are specific for the unlabeled immunoglobulin) or other suitable reagent (e.g., labeled protein A).

In one embodiment, the antibodies or fragments of the present invention can be utilized in enzyme immunoassays, wherein the subject antibody or fragment, or second antibodies, are conjugated to an enzyme. When a biological sample comprising a mammalian CCR1 protein is combined with the subject antibodies, binding occurs between the antibodies and CCR1 protein. In one embodiment, a sample containing cells expressing a mammalian CCR1 protein, such as human blood, is combined with the subject antibodies, and binding occurs between the antibodies and cells bearing a human CCR1 protein comprising an epitope recognized by the antibody. These bound cells can be separated from unbound reagents and the presence of the antibody-enzyme conjugate specifically bound to the cells can be determined, for example, by contacting the sample with a substrate of the enzyme which produces a color or other detectable change when acted on by the enzyme. In another embodiment, the subject antibodies can be unlabeled, and a second, labeled antibody can be added which recognizes the subject antibody.

Kits for use in detecting the presence of a mammalian CCR1 protein in a biological sample can also be prepared. Such kits will include an antibody or functional fragment thereof which binds to a mammalian CC-chemokine receptor 1 or portion of said receptor, as well as one or more ancillary reagents suitable for detecting the presence of a complex between the antibody or fragment and CCR1 or portion thereof. The antibody compositions of the present invention can be provided in lyophilized form, either alone or in combination with additional antibodies specific for other epitopes. The antibodies, which can be labeled or unlabeled, can be included in the kits with adjunct ingredients (e.g., buffers, such as Tris, phosphate and carbonate, stabilizers, excipients, biocides and/or inert proteins, e.g., bovine serum albumin). For example, the antibodies can be provided as a lyophilized mixture with the adjunct ingredients, or the adjunct ingredients can be separately provided for combination by the user. Generally these adjunct materials will be present in less than about 5% weight based on the amount of active antibody, and usually will be present in a total amount of at least about 0.001% weight based on antibody concentration. Where a second antibody capable of binding to the monoclonal antibody is employed, such antibody can be provided in the kit, for instance in a separate vial or container. The second antibody, if present, is typically labeled, and can be formulated in an analogous manner with the antibody formulations described above.

Similarly, the present invention also relates to a method of detecting and/or quantitating expression of a mammalian CCR1 or a portion of the receptor by a cell, in which a composition comprising a cell or fraction thereof (e.g., membrane fraction) is contacted with an antibody or functional fragment thereof (e.g., 2D4) which binds to a mammalian CCR1 or portion of the receptor under conditions appropriate for binding of the antibody or fragment thereto, and binding is monitored. Detection of the antibody, indicative of the formation of a complex between antibody and CCR1 or a portion thereof, indicates the presence of the receptor. Binding of antibody to the cell can be determined as described above under the heading "Binding Assays", for example. The method can be used to detect expression of CCR1 on cells from an individual (e.g., in a sample, such as a body fluid, such as blood, saliva or other suitable sample). The level of expression of CCR1 on the surface of T cells or monocytes can also be determined, for instance, by flow cytometry, and the level of expression (e.g., staining intensity) can be correlated with disease susceptibility, progression or risk.

Chemokine receptors function in the migration of leukocytes throughout the body, particularly to inflammatory sites. Inflammatory cell emigration from the vasculature is regulated by a three-step process involving interactions of leukocyte and endothelial cell adhesion proteins and cell specific chemoattractants and activating factors (Springer, T. A., *Cell*, 76:301–314 (1994); Butcher, E. C., *Cell*, 67:1033–1036 (1991); Butcher, E. C. and Picker, L. J., *Science* (Wash. D.C.), 272:60–66 (1996)). These are: (a) a low affinity interaction between leukocyte selectins and endothelial cell carbohydrates; (b) a high-affinity interaction between leukocyte chemoattractant receptors and chemoattractant/activating factors; and (c) a tight-binding between leukocyte integrins and endothelial cell adhesion proteins of the immunoglobulin superfamily. Different leukocyte subsets express different repertoires of selectins, chemoattractant receptors and integrins. Additionally, inflammation alters the expression of endothelial adhesion proteins and the expression of chemoattractant and leukocyte activating factors. As a consequence, there is a great deal of diversity for regulating the selectivity of leukocyte recruitment to extravascular sites. The second step is cricial in that the activation of the leukocyte chemoattractant receptors is thought to cause the transition from the selectin-mediated cell rolling to the integrin-mediated tight binding. This results in the leukocyte being ready to transmigrate to perivascular sites. The chemoattractant/chemoattractant receptor interaction is also crucial for transendothelial migration and localization within a tissue (Campbell, J. J., et al., *J. Cell Biol.*, 134:255–266 (1996); Carr, M. W., et al., *Immunity*, 4:179–187 (1996)). This migration is directed by a concentration gradient of chemoattractant leading towards the inflammatory focus.

CCR1 has an important role in leukocyte trafficking. It is likely that CCR1 is a key chemokine receptor for T cell or T cell subset or monocyte migration to certain inflammatory sites, and so anti-CCR1 mAbs can be used to inhibit (reduce or prevent) T cell or monocyte migration, particularly that associated with T cell dysfunction, such as autoimmune disease or allergic reactions, or with monocyte-mediated disorders such as atherosclerosis. Accordingly, the antibodies and fragments thereof of the present invention can also be used to modulate receptor function in research and therapeutic applications. For instance, the antibodies and functional fragments described herein can act as inhibitors to inhibit (reduce or prevent) (a) binding (e.g., of a ligand, an inhibitor or a promoter) to the receptor, (b) a receptor signaling function, and/or (c) a stimulatory function. Antibodies which act as inhibitors of receptor function can block ligand or promoter binding directly or indirectly (e.g., by causing a confonnational change). For example, antibodies can inhibit receptor function by inhibiting binding of a ligand, or by desensitization (with or without inhibition of binding of a ligand). Antibodies which bind receptor can also act as agonists of receptor function, triggering or stimulating a receptor function, such as a signaling and/or a stimulatory function of a receptor (e.g., leukocyte trafficking) upon binding to receptor.

Thus, the present invention provides a method of inhibiting leukocyte trafficking in a mammal (e.g., a human patient), comprising administering to the mammal an effective amount of an antibody or functional fragment of the present invention. Administration of an antibody or fragment of the present invention can result in amelioration or elimination of the disease state.

The antibody of the present invention, or a functional fragment thereof, can also be used to treat disorders in which activation of the CCR1 receptor by binding of chemokines is implicated. For example, the antibodies or functional fragments thereof (e.g., 2D4 or functional fragments thereof) can be used to treat allergy, atherogenesis, anaphylaxis, malignancy, chronic and acute inflammation, histamine and IgE-mediated allergic reactions, shock, and rheumatoid arthritis, atherosclerosis, multiple sclerosis, graft rejection, ischemia/reperfusion injury, fibrotic disease, asthma, and inflammatory glomerilopathies.

Diseases or conditions of humans or other species which can be treated with inhibitors of CCR1 receptor function (including antibodies or suitable fragments thereof) include, but are not limited to, those described in Attorney Docket No. LKS98-13, "Methods For Preventing Graft Rejection and Ischemia-Reperfusion Injury", by Wayne W. Hancock, filed Jan. 29, 1999, and Attorney Docket No. LKS98-17, "Method of Treating Demyelinating Inflammatory Disease Using CCR1 Antagonists", by James B. Rottman and Wayne W. Hancock, filed Jan. 29, 1999, the entire teachings of both of which are incorporated herein in their entirety, and the following:

inflammatory or allergic diseases and conditions, including respiratory allergic diseases such as asthma, allergic rhinitis, hypersensitivity lung diseases, hypersensitivity pneumonitis, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); anaphylaxis or hypersensitivity responses, drug allergies (e.g., to penicillin, cephalosporins), insect stinig allergies; inflammatory bowel diseases, such as Crohn's disease and ulcerative colitis; spondyloarthropathies; sclerodenna; psoriasis and inflammatory dermatoses such as dermnatitis, eczema, a topic dermatitis, allergic contact dermatitis, urticaria; vasculitis (e.g., necrotizing, cutaneous, and hypersensitivity vasculitis);

autoimmune diseases, such as arthritis (e.g., rheumatoid arthritis, psoriatic arthritis), demyelinating disorders (e.g., multiple sclerosis), systemic lupus erythematosus, myasthenia gravis, juvenile onset diabetes, nephritides such as glomerulonephritis, autoimmune thyroiditis, Behcet's disease;

chronic or acute graft rejection (e.g., in transplantation), including allograft rejection or graft-versus-host disease, and graft-associated arteriosclerosis;

atherosclerosis;

cancers with leukocyte infiltration of the skin or organs;

other diseases or conditions (including CCR1 -mediated diseases or conditions), in which undesirable inflammatory responses are to be inhibited can be treated, including, but not limited to, ischemia/reperfusion injury, certain hematologic malignancies, cytokine-induced toxicity (e.g., septic shock, endotoxic shock), polymyositis, dermatomyositis, and granulomatous diseases including sarcoidosis.

Diseases or conditions of humans or other species which can be treated with promoters of CCR1 receptor function (including antibodies or fragments thereof), include, but are not limited to:

immunosuppression, such as that in individuals with immunodeficiency syndromes such as AIDS, individuals undergoing radiation therapy, chemotherapy, therapy for autoimmune disease or other drug therapy (e.g., corticosteroid therapy), which causes immunosuppression; and immunosuppression due congenital deficiency in receptor function or other causes.

Anti-CCR1 antibodies of the present invention can block the binding of one or more chemokines, thereby blocking the downstream cascade of one or more events leading to the above disorders.

Modes of Administration

One or more antibodies or fragments of the present invention can be administered to an individual by an appropriate route, either alone or in combination with (before, simultaneous with, or after) another drug or agent. For example, the antibodies of the present invention can also be used in combination with other monoclonal or polyclonal antibodies (e.g., in combination with antibodies which bind other chemokine receptors, including, but not limited to, CCR2, CCR3, CCR4 and CCR5) or with existing blood plasma products, such as commercially available gamma globulin and immune globulin products used in prophylactic or therapeutic treatments. The antibodies or fragments of the present invention can be used as separately administered compositions given in conjunction with antibiotics and/or antimicrobial agents. The antibodies or fragments of the invention can also be administered in combination with anti-viral agents, immunosuppressive agents (e.g., calcineurin inhibitors, such as cyclosporin A; glucocorticoids, such as prednisone or methylprednisolone; and nucleic acid synthesis inhibitors, such as azathioprine or mycophenolic acid), cytokines, such as interferon and Th2-producing cytokines, and hormones, such as adrenocorticotropic hormone.

An effective amount of an antibody or fragment (i.e., one or more antibodies or fragments) is administered. An effective amount is an amount sufficient to achieve the desired therapeutic (including prophylactic) effect, under the conditions of administration, such as an amount sufficient for inhibition of a CCR1 fuinction, and thereby, inhibition of an inflammatory response or HIV infection, or an amount sufficient for promotion of a CCR1 function, as indicated.

A variety of routes of administration are possible including, but not necessarily limited to, oral, dietary, topical, parenteral (e.g., intravenous, intra arterial, intramuscular, subcutaneous injection), inhalation (e.g., intra bronchial, intraocular, intranasal or oral inhalation, intranasal drops), intraocular, depending on the disease or condition to be treated. Other suitable methods of administration can also include rechargeable or biodegradable devices and slow release polymeric devices. The pharmaceutical compositions of this invention can also be administered as part of a combinatorial therapy with other agents.

Formulation of an antibody or fragment to be administered will vary according to the route of administration and formulation (e.g., solution, emulsion, capsule) selected. An appropriate pharmaceutical composition comprising an antibody or functional fragment thereof to be administered can be prepared in a physiologically acceptable vehicle or carrier. A mixture of antibodies and/or fragments can also be used. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. A variety of appropriate aqueous carriers arc known to the skilled artisan, including water, buffered water, buffered saline, polyols (e.g., glycerol, propylene glycol, liquid polyethylene glycol), dextrose solution and glycine. Intravenous vehicles can include various additives, preservatives, or fluid, nutrient or electrolyte replenishers (See, generally, *Remington's Pharniacezitical Science*, 16th Edition, Mack, Ed. 1980). The compositions can optionally contain pharmaceutically acceptable auxiliary substances as required to approximate physiological conditions such as pH adjusting and buffering agents and toxicity adjusting agents, for example, sodium acetate, sodium chloride, potassium chloride, calcium chloride and sodium lactate. The antibodies and fragments of this invention can be lyoplilized for storage and reconstituted in a suitable carrier prior to use according to art-known lyophilization and reconstitution techniques. The optimum concentration of the active ingredient(s) in the chosen medium can be determined empirically, according to procedures well known to the skilled artisan, and will depend on the ultimate pharmaceutical formulation desired. For inhalation, the antibody or fragment can be solubilized and loaded into a suitable dispenser for administration (e.g., an atomizer, nebulizer or pressurized aerosol dispenser).

The following Examples are offered for the purpose of illustrating the present invention and are not to be construed to limit the scope of this invention. The contents of all references, patents and published patent applications cited throughout this application are hereby incorporated by reference.

EXAMPLES

Methods

Cells, Cell Lines, and Tissue Culture

Normal human blood leukocytes were isolated as described (Heath et al., *J. Clin. Invest.* 99:178 (1997)). To generate CD3 blasts, $2 \times 10^6$ PBMC/ml in RPMI-1640 plus 10% FCS were added to tissue culture plates first coated with the anti-CD3 antibody TR66. After 4–6 days blasts were removed to fresh media and supplemented with IL-2 (kindly provided by Antonio Lanzavecehia, Basel Institute for Immunology, Basel, Switzerland) at 50 uits/ml. In some cases, 10 ng/ml of IFNα (Peprotech, Rocky Hill, N.J.) was added to the cultures 4 days after stimulation.

Human CCR1 was expressed in the murine pre-B cell line L1-2 as described previously (Honda et al., *J. Immunol.* 152:4026 (1994)). In brief, primer sequences for the coding regions and 3'UTR of CCR1 were obtained from Genbank (accession number L09320) and the gene amplified by rt-PCR from human peripheral blood. The amplified product was directionally cloned into the expression vector pMRB-101 and L1-2 cells were transfected with linearized plasmid and selected by growth in mycophenolic acid containing medium. Resistant cells were stained with anti-FLAG Ab M1 (IBI-A Kodak Co., New Haven, Conn.) and sorted by flow cytometry. After several rounds of sorting, the cells were further selected by chemotaxis to 10 nM MIP-1α.

mAb Production and Flow Cytometry mAbs reactive with CCR1 were generated by immunizing mice with $1 \times 10^7$ CCR1 L1-2 transfectants intraperitoneally at 2 week intervals. Four days after the last immunization, mice were sacrificed, the spleen removed and cell fusion performed using the cell line SP2/O, as described (Coligan et al., *Current Protocols in Imuniology* 2.5.2 (1992)). Specific mAbs reactive with CCR1 were identified by flow cytometry using a FACScan® (Becton Dickinson & Co., Mountain View, Calif.) as described below. Antibodies were screened for immunofluorescent staining of CCR1 transfectant without staining of untransfected cells or cells transfected with all other human chemokine receptors. The CCR1 specific mAb described in this report, 2D4, was isotyped by ELISA (Southern Biotechnology, Birmingham, Ala.) and determined to be IgGI. The 2D4 hybridoma can be cultivated in 90% DMEM, 10% fetal calf serum, and 100 ng/ml IL-6.

Mouse mAbs to human CCR3, CCR5 and CXCR3 have been described (Qin et al., *J. Clin. Invest.* 101:746 (1998); (Heath et al, *J. Clin. Invest.* 99:178 (1997)). Flourochrome conjugated mAbs to CD4, CD8, CD19, CD25, CD26, CD45RO, CD45RA and biotinylated anti-IgE were supplied by Pharmingen (La Jolla, Calif.). To assess reactivity of mAbs against transfected cells or leukocytes, indirect immunofluorescence and flow cytometry were used. Cells were washed once with PBS, and resuspended in 100 µl PBS containing 2% human serum and 0.1% sodium azide (staining buffer), 5 µg/ml purified antibody, 5 µg/ml isotype matched control mAb (Sigma Chemical Co., St. Louis, Mo.) or 50 µl hybridoma culture supernatant. After 20 minutes at 4° C., cells were washed twice with staining buffer, and resuspended in 50 µl FITC-conjugated affinity purified F(ab')$_2$ goat anti-mouse IgG (Jackson ImmunoResearch Laboratories). After 20 min, cells were washed twice in staining buffer and analyzed by FACScan® to determine the level of surface expression. Propidium iodide was used to exclude dead cells. For multicolor analysis cells were first stained with anti-CCR1 mAb 2D4, followed by anti-mouse-APC (Pharmingen). After blocking with mouse serum, PE-, FITC- or Cy3-conjugated mAbs were used together to stain cells. The results were analyzed by FACScan® using electronic gating and compensation.

Chemokines, Chemotaxis Assays, and Ligand Binding Assay

Recombinant human chemokines were obtained from Peprotech (Rocky Hill, N.J.) or R&D Systems (Minneapolis, Minn.) except for IL-8 which was produced recombinantly at LeukoSite (Wu et al., *J. Biol. Chem.* 271:31202 (1996)). Chemotaxis of human PMBC or CD3 blasts was assessed in transendothelial migration assays (Carr et al., *Proc. Nail. Acatl. Sci. USA* 91:3652 (1994)) using the cell line ECV304 as described (Ponath et al., *J. Clin. Invest.* 97:604 (1996)). Cells that migrated to the bottom chamber were collected, and relative cell counts were obtained using the FACScan®. Chemotaxis of human eosinophils and neutrophils was carried out using 96-well chemotaxis plates (Neuro Probe, Gaithersburg, Md). Twenty nine µl of appropriately diluted chemokine in RPMI-1640 plus 0.5% SBA was added to the wells which were then covered with a 2 micron filter membrane. $5 \times 10^4 – 1 \times 10^5$ cells in 25 µl were added onto the filter above each well. The plate was incubated for 25–30 minutes at 37° C., the filter removed and plate frozen at −80° C. for 30 minutes. After thawing, 6 µl of CyQuant (Molecular Probes, Eugene, Oreg.) solution was added to the wells and the plate read by a fluorescence plate reader. The migration is presented as the mean of Relative Fluorescence Unit (RFU) which is proportional to the number of migrated cells.

$^{125}$I-labeled chemokines were obtained from NEN (Boston, Mass.). Chemokine binding to target cells was carried out as described previously (Ponath et al., *J. Exp. Med.* 183:2437 (1996)). Briefly, cells were resuspended in binding buffer (50 mM HEPES, 1 mM $CaCl_2$, 0.5% BSA) and incubated with radiolabeled ligand in the presence or absence of competitors. After 60 minutes at 37° C., cells were washed 3 times in binding buffer supplemented with 0.5 N NaCl and pellets counted. All experiments were carried out in duplicate and repeated at least three times. Curve fit and concentrations that inhibit 50% specific binding ($IC_{50}$) were calculated by KaleidaGraph software (Synergy Software, Reading, Pa.)

Calcium Flux Assay

Freshly isolated human PBMC were labeled with Fluo-3 and responses to various chemokines measured on a FACScan® as described previously (Ponath et al., *J. Clin. Invest.* 97:604 (1996)). Different leukocyte populations were gated by forward versus side scatters and a steady baseline fluorescence of FL1 was first obtained. The cells were then stimulated with various chemokines and the change of fluorescence intensity was recorded and plotted during the time course. When anti-receptor antibodies were used, the cells were incubated with mAb for 5 minutes prior to addition of chemokine.

Results

Generation of a Blocking mAb against CCR1

Figure 1B:
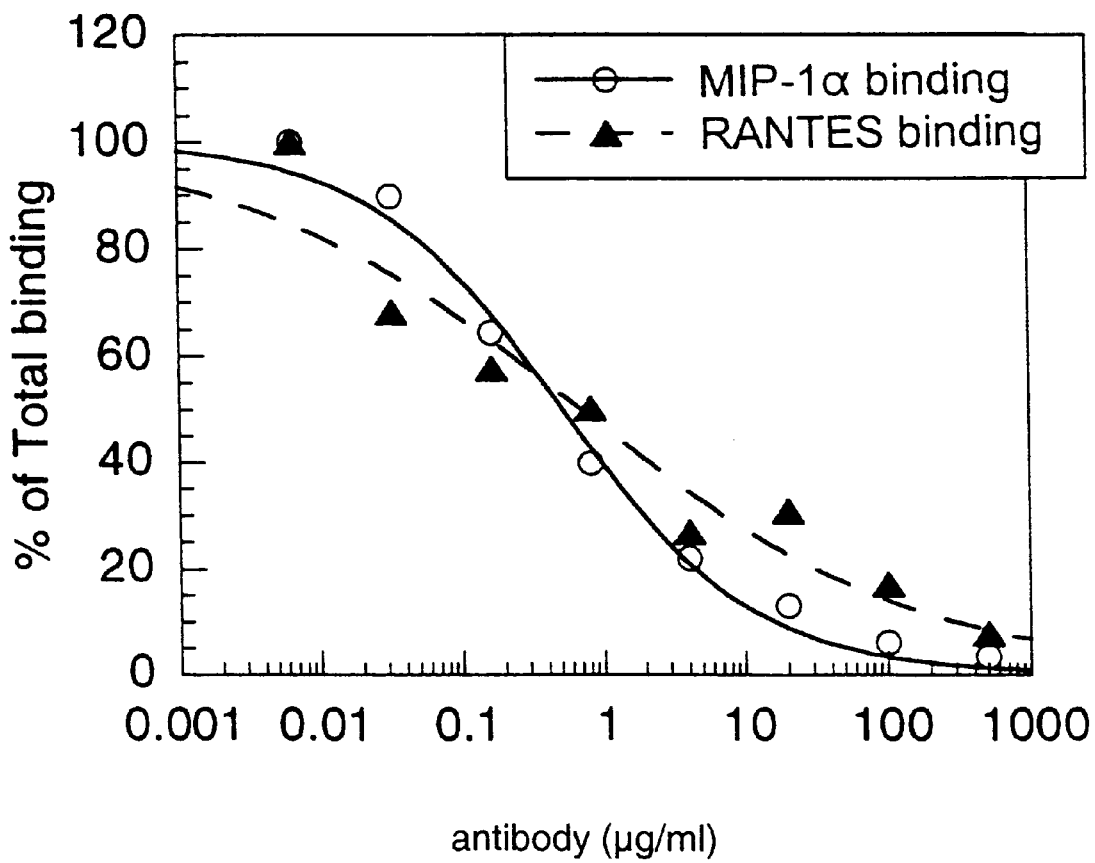

A monoclonal antibody, termed 2D4, was generated by immunizing mice with cells expressing high levels of transfected human CCR1. This mAb stained cells transiently transfected with CCR1 cDNA and several independently derived stable CCR1 transfected cell lines, but not parental cells or cells transfected with other chemokine receptors (FIG. 1A). When 2D4 was added to radiolabeled ligand binding assays, it completely inhibited binding of $^{125}$I-MIP-1α with an $IC_{50}$ of 3.4 nM (0.5 µg/ml) (FIG. 1B). In the same set of experiments $^{125}$I-MIP-1α binding to CCR1 was competed by unlabeled MIP-1α and RANTES with an $IC_{50}$ of 1.1 nM and 2.5 nM, respectively. 2D4 inhibited $^{125}$I-RANTES binding to CCR1 transfectants with an $IC_{50}$ of 4.5 nM (0.7 µg/ml) (FIG. 1B).

CCR1 is the Predominant Chemokine Receptor for MIP-1α and RANTES on Monocytes

Figure 2A:
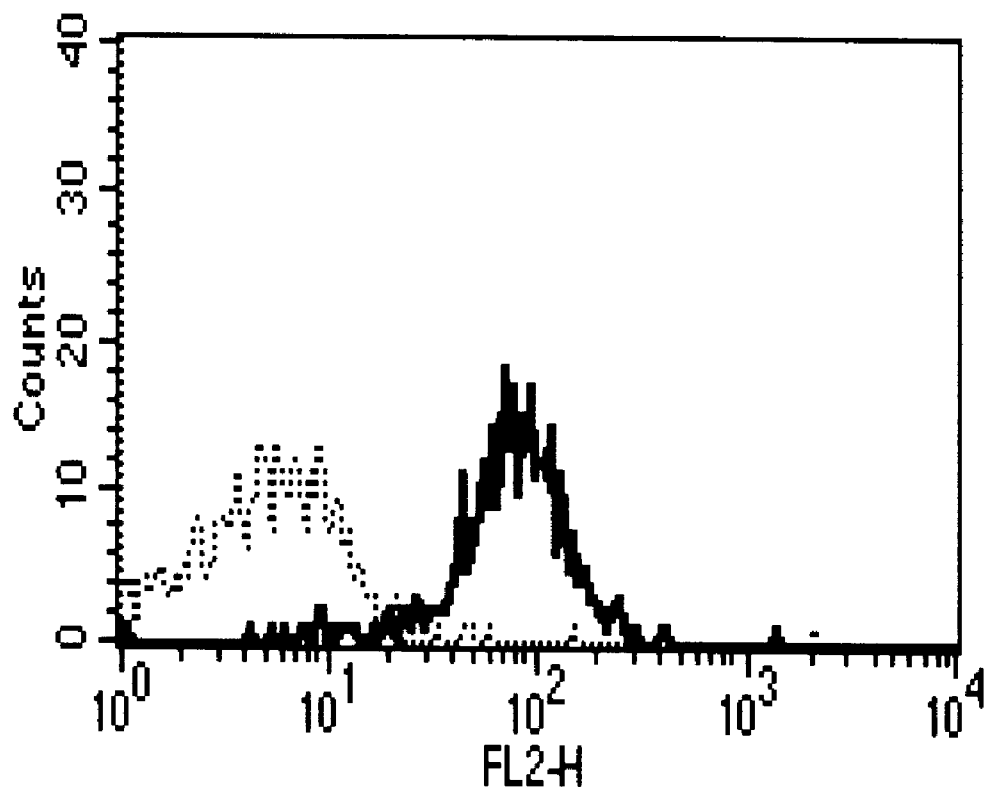
FIGS. 2A and 2B show that monocyte responses to MIP-1α and RANTES are CCR1 -dependent.
Figure 2B:
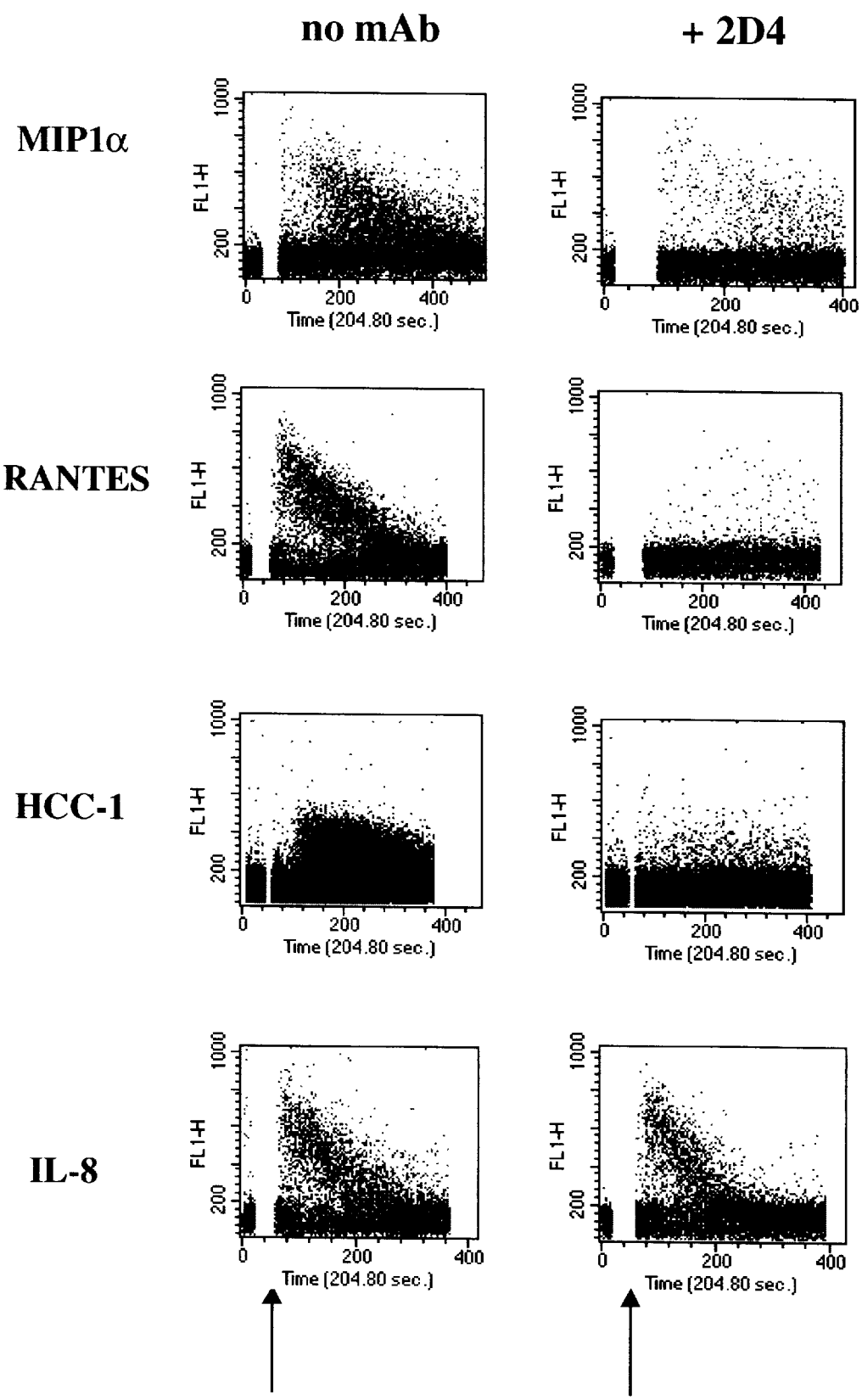

All peripheral blood monocytes were brightly stained with anti-CCR1 mAb 2D4 (FIG. 2A). Mobilization of $[Ca^{2+}]_i$ in monocytes induced by 20 nM MIP-1α or 20 nM RANTES was completely blocked by 50 µg/ml of 2D4 while the response to IL-8 (FIG. 2B) or MCP-1 was unaffected by this antibody. HCC-1, a chemokine recently reported to be a ligand for CCR1, induced a weak calcium response at a concentration of 100 nM, which was completely inhibited by 2D4 as well. 2D4 only partially inhibited the activities of MCP-3, a chemokine which has been shown to mediate functions through several chemokine receptors including CCR2 on monocytes (Franci et al., *J. Immunol.* 154:6511 (1995)). The $Ca^{2+}$ flux data correlated with results from chemotaxis assays which showed that MIP-1α and RANTES induced monocyte migration could be completely blocked by 2D4 while there was no effect on monocyte chemotaxis to MCP-1, a CCR2 specific ligand (Table 1). Only minimal monocyte chemotaxis was induced by MIP-1α, a ligand for CCR5 but not CCR1.

TABLE 1

Inhibition of Monocyte Chemotaxis by Anti-CCR1 mAb

| Chemokine | mAb | Specificity | # of Migrated Cells |
|---|---|---|---|
| MCP-1 | no |  | 278 ± 76 |
| MCP-1 | 2D4 | CCR1 | 205 ± 24 |
| MCP-1 | 2D7 | CCR5 | 250 ± 13 |
| MIP-1α | no |  | 192 ± 21 |
| MIP-1α | 2D4 | CCR1 | 22 ± 11 |
| MIP-1α | 2D7 | CCR5 | 127 ± 45 |
| RANTES | no |  | 405 ± 38 |
| RANTES | 2D4 | CCR1 | 32 ± 18 |
| RANTES | 2D7 | CCR5 | 392 ± 44 |
| MIP-1β | no |  | 28 ± 10 |
| MIP-1β | 2D4 | CCR1 | 29 ± 15 |
| MIP-1β | 2D7 | CCR5 | 18 ± 4 |
| Media | no |  | 12 ± 4 |

Freshly isolated human PBMC were used in chemotaxis assay with 10 nM of MCP-1, MIP-1α, RANTES and MIP-1β. Migrated monocytes cells were counted by flow cytometry using forward and side scatters.

CCR1 is Expressed on a Subset of Memory T Lymphocytes

Figure 3A:
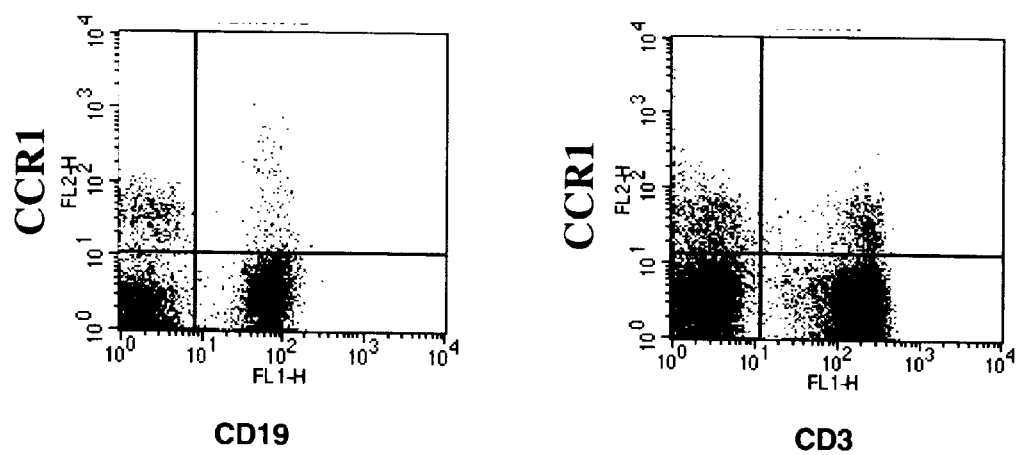
FIGS. 3A and 3B show CCR1 expression on peripheral blood lymphocytes.
Figure 3B:
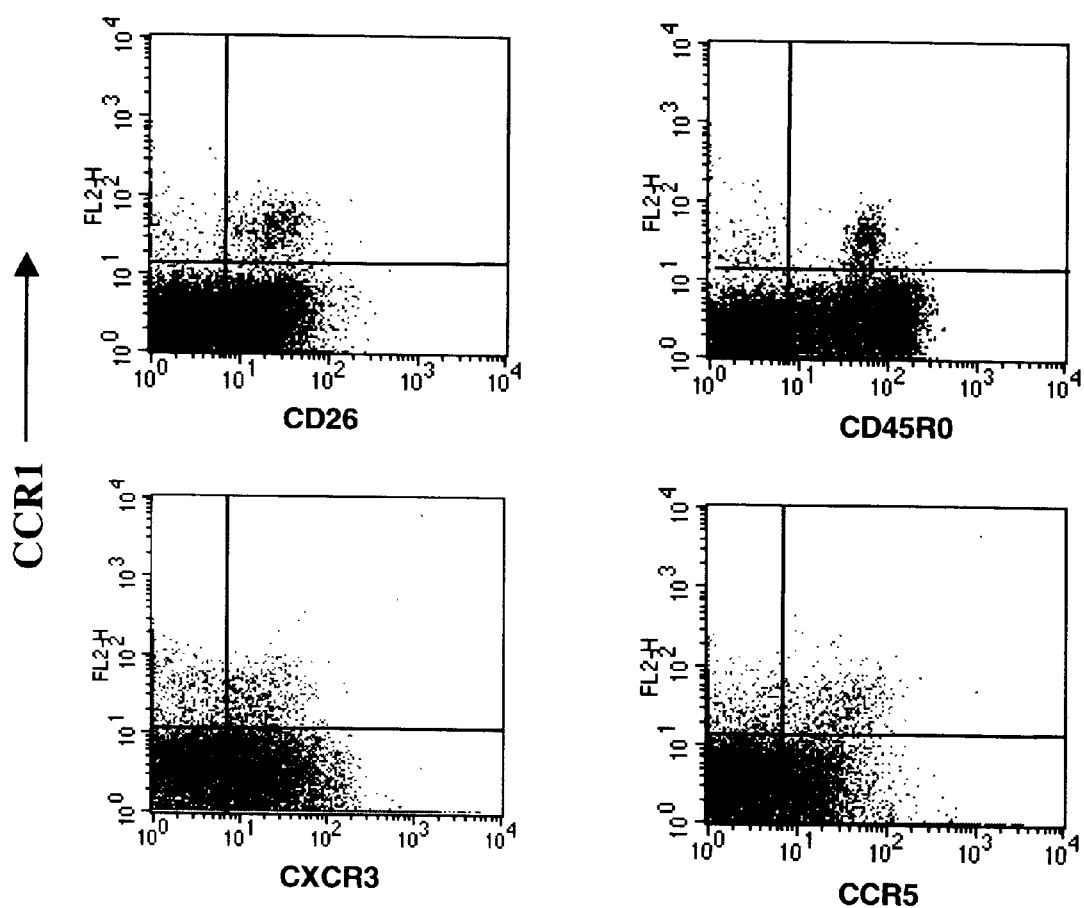

In peripheral blood, 2D4 consistently stained a small percentage of CD3+ cells, ranging from 1–5% depending on the individual. Analysis by multicolor flow cytometry showed that CCR1+ T cells were CD45RO+ CD26+, a phenotype characteristic of post-activation memory T cells (FIG. 3A and 3B). All CCR1+ T cells were contained within the CCR5+ and CXCR3+ T cell population which comprise 30–50% of total peripheral blood T cells (FIG. 3B). 2D4 also stained consistently a small percentage of B cells (0.5%–5%, n=6). CD56+NK cells were virtually negative when stained with 2D4.

CCR1 Expression on Activated T Cells

Figure 4:
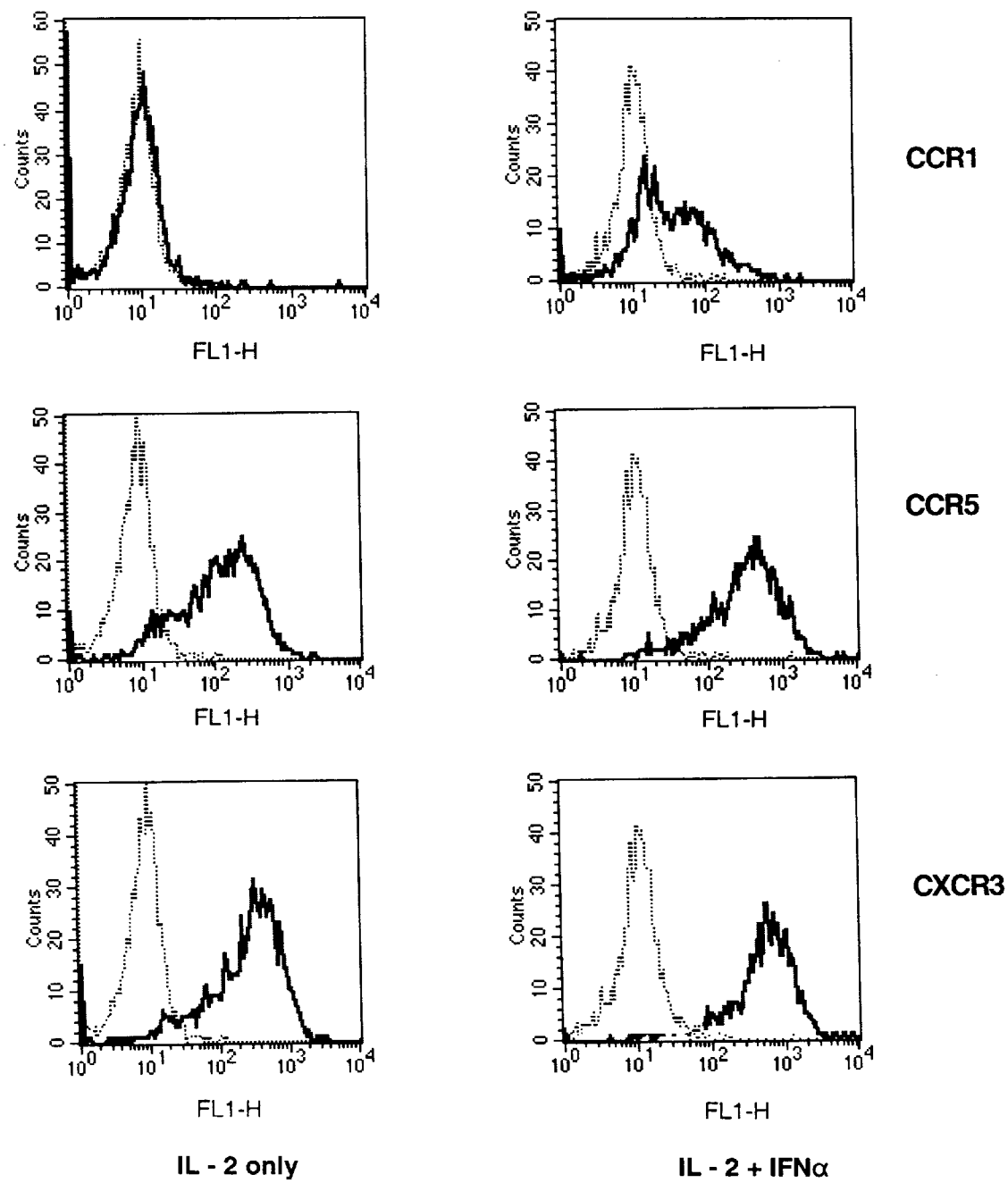
FIG. 4 shows CCR1 expression on activated T cells. Human PBMC were stimulated with anti-CD3 and IL-2 in the absence or presence of IFNα. Cells were cultured for ten days then stained with mAbs to CCR1, CCR5 and CXCR3 as indicated (solid line). Negative controls (dotted line) were stained with an irrelevant mouse IgG1. Data obtained from day 14 staining gave a similar profile.
Figures 5A, 5B:
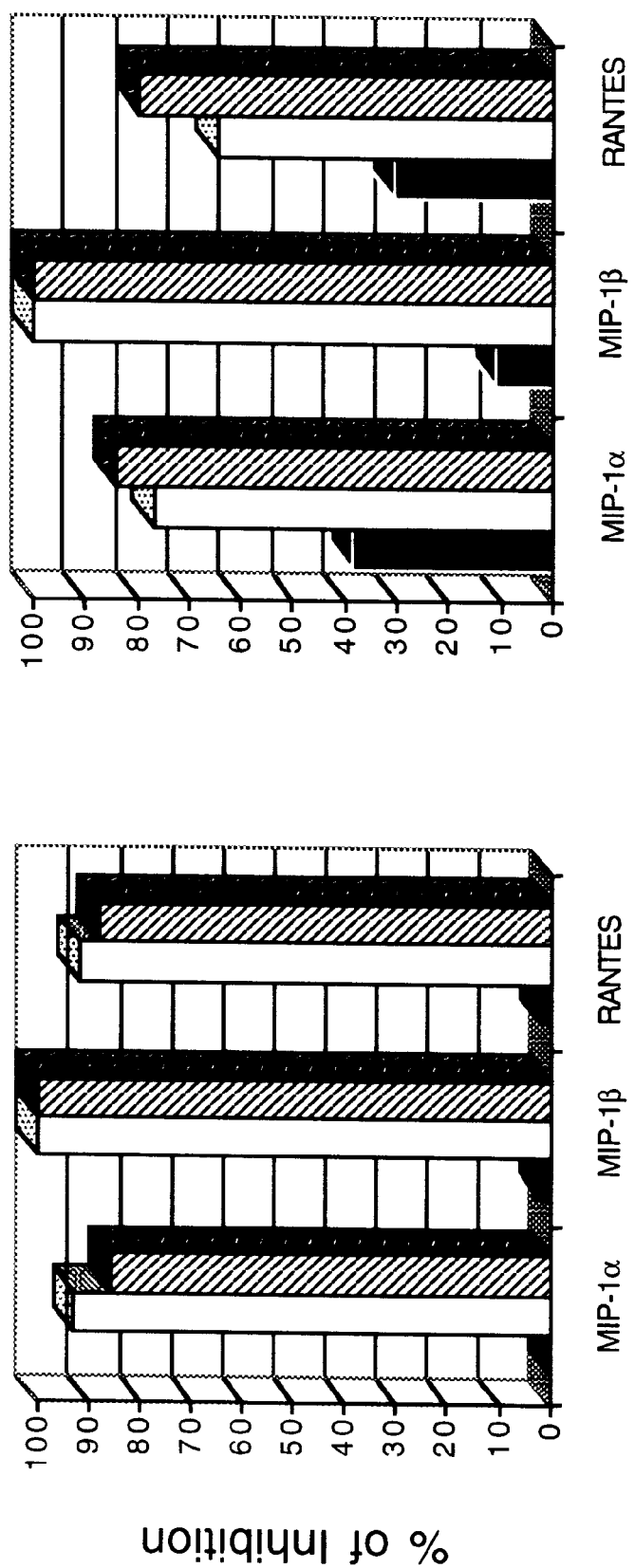
FIGS. 5A and 5B show inhibition of chemotaxis with anti-CCR1 mAb 2D4. Activated T cells were used in a chemotaxis assay to 50 nM of MIP-1α, MIP-1β or RANTES in the presence of 50 μg/ml 2D4 (anti-CCR1, solid bar), 2D7 (anti-CCR5, blank bar) or both mAbs at 50 μg/ml each (hatched bar).

Activated T cells respond much more vigorously to chemokines than resting T cells and also show increased expression of a number of chemokine receptors (Qin et al., *J. Clin. Invest.* 101:746 (1998); Loetscher et al., *J. Exp. Med.* 184:569 (1996); Wu et al., *J. Exp. Med.* 186:1373 (1997)), CCR5 and CXCR3 in particular. To determine if CCR1 is also upregulated in a similar fashion, peripheral blood T cells were activated by aniti-CD3 and IL-2 and cells were analyzed at various times for chemokine receptor expression by flow cytometry. During the first three days of stimulation with anti-CDS, most chemokine receptors were down-modulated from the cell surface, a phenomenon previously have observed (Qin et al., *J. Clin. Invest.* 101:746 (1998); Loetscher et al., *J. Exp. Med.* 184:569 (1996)). the expression of CXCR3 and CCR5 began to increase after day 4 and reached maximum levels at days 5–6 for CXCR3 and days 12–14 for CCR5. However, the expression of CCR1 remained undetectable by flow cytometry throughout this period of time (Table 2 and FIG. 4). Chemotaxis assays confirmed that CCR1 did not play a significant role in MIP-1α or RANTES induced migration of the activated T cells and demonstrated that the majority of migration was mediated by CCR5 (FIGS. 5A and 5B). Data in FIG. 5A show that 2D4 failed to inhibit chemotaxis of T cell blast to MIP-1α or RANTES while the anti-CCR5 mAb 2D7 blocked both MIP-1β and RANTES induced migration as well as MIP-1α induced chemotaxis by >90%.

Recently it was reported the IFNα could increase CCR1 mRNA levels when T cells were cultured under Th1 or Th2 polarizing conditions (Sallusto et al., *J. Exp. Med.* 187:875 (1998)). In the present study, the ability of IFNα to upregulate CCR1 surface expression in bulk culture where expression was usually downregulated was assessed. In all donors tested, an increase CCR1 expression of activated T cells was detected when cultured in the presence of IFNα. Data in Table 2 show that CCR1 began to appear on IFNα treated cells by day 7, and gradually reach maximum level between days 10–14, i.e. 6–10 days after the addition of IFNA (Table 2 and FIG. 4). CCR1 expressed on the IFNα treated T cells made a significant functional contribution to the chemotactic potential these cells as demonstrated by receptor blockade with mAbs in migration assays to MIP-1α and RANTES (FIG. 5B). In the presence of IFNα, the anti-CCR1 could inhibit the cell migration to MIP-1α by 39%, while the anti-CCR5 inhibited migration to MIP-1α by 58%. A combination of anti-CCR1 and anti-CCR5 inhibited chemotaxis by 89%. The anti-CCR1 mAb had no effect on chemotaxis to MIP-1α of CD3 blasts cultured only with IL-2 which could be completely inhibited by 50 μg/ml of anti-CCR5 (FIG. 5A). The anti-CCR1 mAb had no effect on the migration to MIP-1β while the anti-CCR1 mAb inhibited this migration by >95%, irrespective of IFNα treatment.

TABLE 2

Change of Chemokine Receptor Expression During T Cell Activation

| | | Percentage of Positive Cells | | |
|---|---|---|---|---|
| | | CCR1 | CCR5 | CXCR3 |
| Day 0 | | 7.8 | 27.6 | 35.3 |
| Day 4 | | 2.7 | 1.1 | 17.9 |
| Day 7 | IL-2 only | 2.7 | 62.8 | 94.2 |
| | IL-2 + IFNα | 13.7 | 62.7 | 94.3 |
| Day 10 | IL-2 only | 3.4 | 62.5 | 89 |
| | IL-2 + IFNα | 45.1 | 68.3 | 90.1 |
| Day 14 | IL-2 only | 2.3 | 75.9 | 90.2 |
| | IL-2 + IFNα | 83.8 | 87.1 | 84 |

Human PBMC wee stimulated with anti-CD3 mAb on Day 0. On Day 4, cells were split and incubated with IL-2 only or IL-2 and IFNα. Cells were taken at the indicated days and stained for chemokine receptor expression. Data represent results from one of eight donors, all gave similar profile.

Marked Variation of CCR1 Expression on Eosinophils

Figure 6:
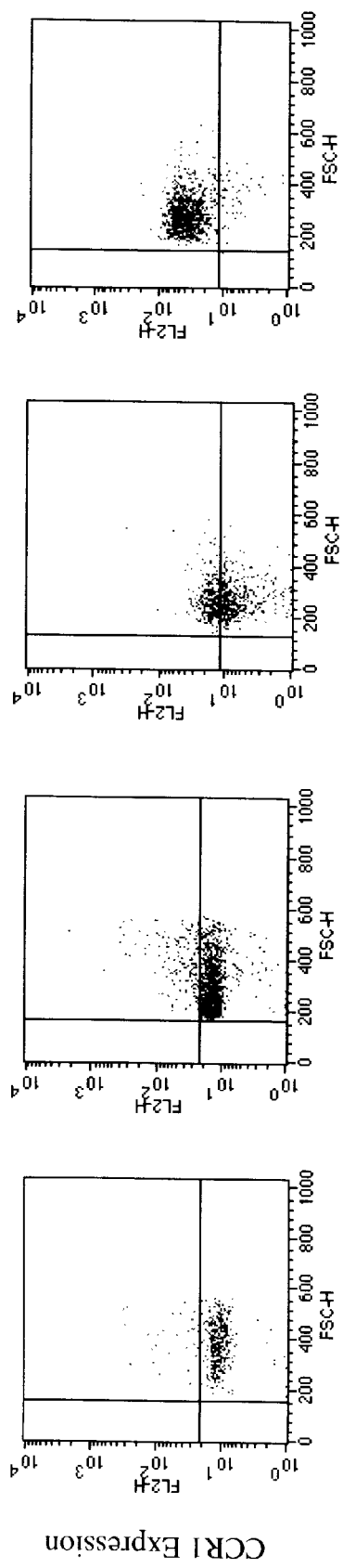
FIG. 6 shows various expression levels of CCR1 on eosinophils. Eosinophils were purified from normal donors and stained with anti-CCR1 mAb 2D4. Dot plots were used to better demonstrate positively stained cells. Data were staining profiles from four different donors to represent the range of CCR1 expression on eosinophils from different individuals.
Figure 7A:
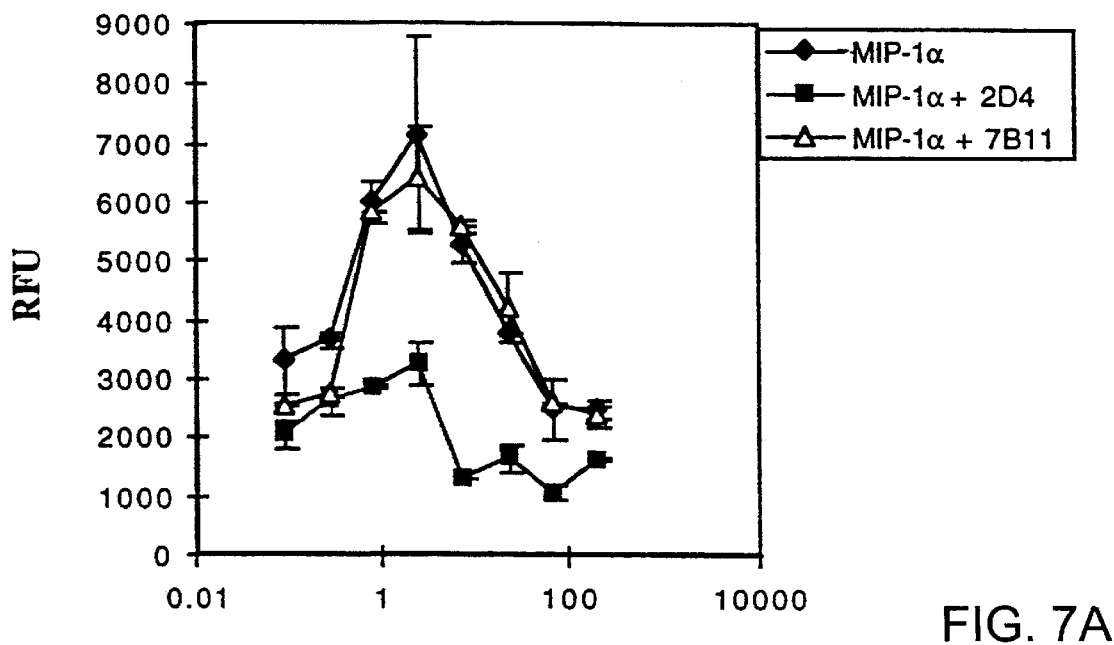
FIGS. 7A and 7B show that eosinophil chemotaxis to MIP-1α can be completely inhibited by anti-CCR1 monoclonal antibody 2D4. Purified eosinophils from a donor that showed >90% CCR1 positive cells were used in chemotaxis assays (Forssmann et al., *FEBS Lett.* 408:211 (1997)) to increasing concentrations of MIP-1α (FIG. 7A) and eotaxin (FIG. 7B), in the presence of anti-CCR1 mAb 2D4 or anti-CCR3 mAb 7B11 at 20 μg/ml. Chemotaxis was carried out in 96-well plates, and migrated cells were measured by a fluorescence plate reader.
Figure 7B:
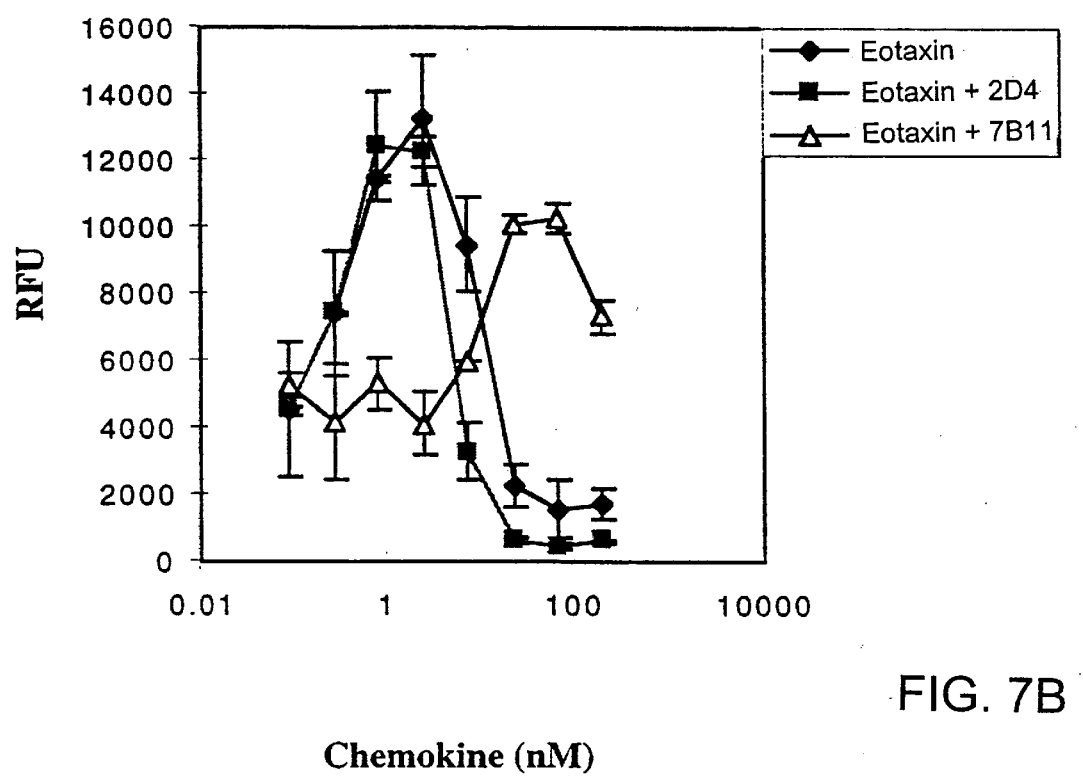

Human eosinophils respond vigorously to eotaxin, RANTES, MCP-3 and MCP-4. Using a blocking mAb to CCR3, a previous study showed (Heath et al., *J. Clin. Invest.* 99:178 (1997)) that these responses were predominantly mediated through CCR3. Although weak responses to MIP-1α have been observed, the expression of CCR1 on human eosinophils has not been well characterized. With the anti-CCR1 mAb, marked donor variation in CCR1 expression on human eosinophils was observed. FIG. 6 represents the staining profile of purified eosinophils from four individuals. The expression of CCR1 ranged from completely negative (Donor #52) to over 95% positive (Donor #5). The expression of CCR3 on these cells was almost >95% positive. Functionally, eosinophils that were completely negative for CCR1 failed to respond to MIP-1α in chemotaxis assays, but those from donors that stained with 2D4 did respond to MIP-1α, although the response was less efficacious than to cotaxin (FIGS. 7A and 7B). The limited number of donor samples analyzed to date and the weak chemotactic response of those donors to MIP-1α does not permit statistical analysis of the general pattern of CCR1 expression on eosinophils among a population nor does it allow the establishment of a strong correlation between the percentage of CCR1+ eosinophils and their responsiveness to MIP-α at this time. However, it should be noted that among all donors tested, eotaxin was significantly more potent than MIP-1α in eliciting eosinophil chemotaxis even when CCR1 and CCR3 showed equivalent surface expression.

CCR1 is Expressed on Human Neutrophils

Figure 8:
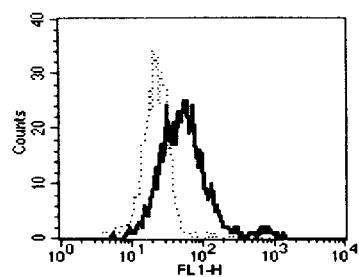
FIG. 8 shows the staining of human blood with anti-CCR1 mAb 2D4. Neutrophils were identified by forward and side scatters.
Figures 9A, 9B, 9C, 9D, 9E, 9F:
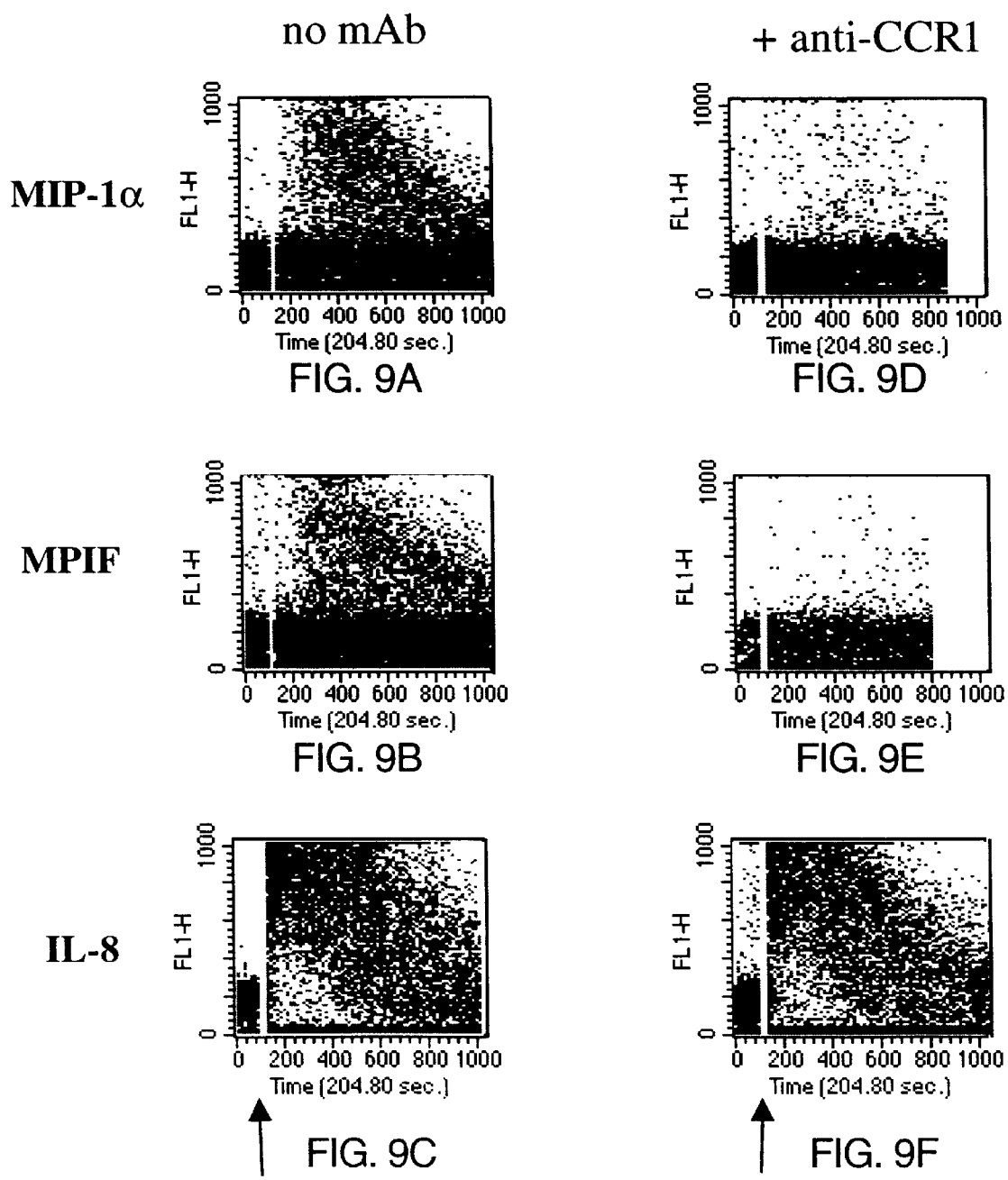
FIGS. 9A–9F show neutrophil intracellular $Ca^{2+}$ mobilization. Fluo-3 loaded neutrophils were stimulated, as indicated by arrow heads, with 100 nM of MIP-1α (FIGS. 9A and 9D), 100 nM MPIF (FIG. 9B and 9E) or 2 nM IL-8 (FIGS. 9C and 9F) in the absence of antibody (9A, 9B and 9C) or in the presence of 50 μg/ml of 2D4 (9D–9F).

Murine neutrophils are known to mount a vigorous chemotactic response to MIP-1α, presumably through CCR1 (Gao et al., *J. Exp. Med.* 185:1959 (1997)). In contrast, human neutrophils migrate very poorly, if at all, to MIP- 1α, although MIP-1α stimulation has been shown induce mobilization of intracellular $Ca^{2+}$ (McColl et al., *J. Immunol.* 150:4550 (1993)). In the current study, anti-CCR1 mAb 2D4 stained 30–50% of neutrophils from all donors tested (FIG. 8) but the CCR1 ligands MIP-1α, RANTES and MPIF failed to induce any neutrophil responses in chemotaxis, degranulation or adhesion assays at concentrations up to 200 nM. In $Ca^{2+}$ flux assays, about 6–8% neutrophils responded to MIP-1α or MPIF stimulation (FIGS. 9A, 9B), in contrast to IL-8 which induced a response by essentially all neutrophils (FIG. 9C). Anti-CCR1 mAb 2D4 completely blocked the $[Ca^{2+}]_i$ mobilization induced by either MIP- 1α or MPIF, but not that by IL-8 (FIGS. 9D–9F).

CCR1 is Expressed on Human Basophils

Basophils are potent inflammatory cells and have ben shown to respond to a number of chemokines and express CCR3 on their surface (Uguccioni et al., *J. Clin. Invest.* 100:1137 (1997)). By double staining human blood with anti-IgE or CCR3, both of which are markers for basophils given their distinct forward and side scatters, CCR1 expression was detected on virtually all basophils (FIG. 11) with anti-CCR1 mAb 2D4.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. An antibody or antigen-binding fragment thereof which binds to a mammalian CC-chemokine receptor 1 or portion of said receptor, wherein said antibody or antigen-binding fragment thereof inhibits binding of a ligand to said receptor, and wherein said antibody or antigen-binding fragment thereof binds the second extracellular loop of said receptor.

2. An antibody or antigen-binding fragment according to claim 1, wherein said antibody or antigen-binding fragment thereof inhibits one or more functions associated with binding of the ligand to the receptor.

3. An antibody or antigen-binding fragment thereof according to claim 1, wherein the second extracellular loop of the receptor consists essentially of the region from amino acid 171 to amino acid 205 of the receptor.

4. An antibody or antigen-binding fragment thereof according to claim 1, wherein the antibody is selected from the group consisting of:
 a) monoclonal antibody 2D4; and
 b) antigen-binding fragments of (a) which bind to mammalian CC-chemokine receptor 1 or a portion thereof.

5. An antibody or antigen-binding fragment thereof according to claim 1, wherein the ligand is a chemokine.

6. An antibody or antigen-binding fragment thereof according to claim 5, wherein the chemokine is selected from the group consisting of MIP-1α, RANTES, MCP-2, MCP-3, leukotactin-1, HCC-1, MPIF and combinations thereof.

7. An antibody or antigen-binding fragment according to claim 1, wherein said antibody or fragment is a monoclonal antibody or fragment thereof.

8. An antibody or antigen-binding fragment according to claim 1, wherein said antibody or fragment is a chimeric antibody or fragment thereof.

9. An antibody or antigen-binding fragment according to claim 1, wherein said antibody or fragment is a human antibody or fragment thereof.

10. An antibody or antigen-binding fragment according to claim 1, wherein said antibody or fragment is a humanized antibody or fragment thereof.

11. An antibody or antigen-binding fragment according to claim 1, wherein said antigen-binding fragment is selected from the group consisting of an Fv fragment, an Fab fragment, an Fab' fragment and an F(ab')$_2$ fragment.

12. An antibody or antigen-binding fragment according to claim 1, wherein said antibody has the epitopic specificity of monoclonal antibody 2D4.

13. The 2D4 hybridoma cell line deposited under ATCC Accession No. HB-12644.

14. A monoclonal antibody produced by the hybridoma cell line according to claim 9 or an antigen-binding fragment thereof.

15. A test kit for use in detecting the presence of a mammalian CC-chemokine receptor 1 or portion thereof in a biological sample comprising
 a) at least one antibody or antigen-binding fragment thereof which binds to a mammalian CC-chemokine receptor 1 or portion of said receptor, wherein said antibody or antigen-binding fragment thereof inhibits bindings of a ligand to the receptor, and wherein said antibody or antigen-binding fragment thereof binds the second extracellular loop of said receptor; and
 b) one or more ancillary reagents suitable for detecting the presence of a complex between said antibody or antigen-binding fragment thereof and said mammalian CC-chemokine receptor 1 or a portion thereof.

16. A test kit according to claim 15, wherein the antibody is selected from the group consisting of
 a) monoclonal antibody 2D4;
 b) antigen-binding fragments of (a) which bind to mammalian CC-chemokine receptor 1 or a portion thereof; and
 c) combinations of the foregoing.

17. A composition comprising an antibody or antigen-binding fragment thereof which binds to a mammalian CC-chemokine receptor 1 or portion of said receptor, wherein said antibody or antigen-binding fragment thereof inhibits binding of a ligand to the receptor and wherein said antibody or antigen-binding fragment thereof binds the second extracellular loop of said receptor, and an optional physiologically acceptable vehicle.

18. An antibody or antigen-binding fragment thereof which binds to a human CC-chemokine receptor 1 or portion of said receptor, wherein said antibody or antigen-binding fragment thereof inhibits binding of a ligand to said receptor and wherein said antibody or antigen-binding fragment thereof binds the second extracellular loop of said receptor.

19. A humanized antibody or antigen-binding fragment thereof which binds to a human CC-chemokine receptor 1 or portion of said receptor, wherein said humanized antibody comprises one or more antigen-binding regions of monoclonal antibody 2D4.

20. A humanized antibody or antigen-binding fragment thereof which binds to a human CC-chemokine receptor 1 or portion of said receptor, wherein said humanized antibody comprises one or more complementarity-determining regions of monoclonal antibody 2D4.

21. A humanized antibody or antigen binding fragment thereof according to claim 20, which comprises six complementarity-determining regions of monoclonal antibody 2D4.

22. A recombinant antibody or antigen-binding fragment thereof which binds to a human CC-chemokine receptor 1 or portion of said receptor, wherein said recombinant antibody comprises one or more complementarity-determining regions of monoclonal antibody 2D4.

23. A recombinant antibody or antigen-binding fragment according to claim 22, wherein said recombinant antibody comprises six complementarity-determining regions of monoclonal antibody 2D4.

24. A composition comprising an antibody or antigen-binding fragment thereof which binds to a human CC-chemokine receptor 1 or portion of said receptor, wherein said antibody or antigen-binding fragment thereof inhibits binding of a ligand to said receptor and wherein said antibody or antigen-binding fragment thereof binds to the second extracellular loop of said receptor, and an optional physiologically acceptable vehicle.

25. A composition comprising a humanized 2D4 antibody or antigen-binding fragment thereof which binds to a human CC-chemokine receptor 1 or portion of said receptor.

26. An antibody or antigen-binding fragment thereof which binds to a mammalian CC-chemokine receptor 1 or portion of said receptor, wherein said antibody or antigen-binding fragment thereof inhibits binding of a ligand to said receptor, and wherein said antibody or antigen-binding fragment thereof can compete with monoclonal antibody 2D4 for binding to said receptor.

27. An antibody or antigen-binding fragment according to claim 26, wherein said antibody or antigen-binding fragment thereof inhibits one or more functions associated with binding of the ligand to said receptor.

28. An antibody or antigen-binding fragment thereof according to claim 26, wherein said mammalian CC-chemokine receptor 1 is a human CC-chemokine receptor 1.

29. An antibody or antigen-binding fragment thereof according to claim 26, wherein the ligand is a chemokine.

30. An antibody or antigen-binding fragment thereof according to claim 29, wherein the chemokine is selected from the group consisting of MIP-1α, RANTES, MCP-2, MCP-3, leukotactin-1, HCC-1 and MPIF.

31. An antibody or antigen-binding fragment according to claim 26, wherein said antibody or fragment is a monoclonal antibody or fragment thereof.

32. An antibody or antigen-binding fragment according to claim 26, wherein said antibody or fragment is a chimeric antibody or fragment thereof.

33. An antibody or antigen-binding fragment according to claim 26, wherein said antibody or fragment is a human antibody or fragment thereof.

34. An antibody or antigen-binding fragment according to claim 26, wherein said antibody or fragment is a humanized antibody or fragment thereof.

35. An antibody or antigen-binding fragment according to claim 26, wherein said antigen-binding fragment is selected from the group consisting of an Fv fragment, an Fab fragment, an Fab' fragment and an F(ab')$_2$ fragment.

36. A test kit for use in detecting the presence of a mammalian CC-chemokine receptor 1 or portion thereof in a biological sample comprising
 a) at least one antibody or antigen-binding fragment thereof which binds to a mammalian CC-chemokine receptor 1 or portion of said receptor, wherein said antibody or antigen-binding fragment thereof inhibits binding of a ligand to said receptor, and wherein said antibody or antigen-binding fragment thereof can compete with monoclonal antibody 2D4 for binding to said receptor; and
 b) one or more ancillary reagents suitable for detecting the presence of a complex between said antibody or antigen-binding fragment thereof and said mammalian CC-chemokine receptor 1 or a portion thereof.

37. A composition comprising an antibody or antigen-binding fragment thereof which binds to a mammalian CC-chemokine receptor 1 or portion of said receptor, wherein said antibody or antigen-binding fragment thereof inhibits binding of a ligand to said receptor and wherein said antibody or antigen-binding fragment thereof can compete with monoclonal antibody 2D4 for binding to said receptor, and an optional physiologically acceptable vehicle.

38. An antibody or antigen-binding fragment thereof which binds to a human CC-chemokine receptor 1 or portion of said receptor, wherein said antibody or antigen-binding fragment thereof inhibits binding of a ligand to said receptor and wherein said antibody or antigen-binding fragment can compete with monoclonal antibody 2D4 for binding to said receptor.

* * * * *

SEQUENCE LISTING

<160> NUMBER OF SEQ ID NOS: 1

<210> SEQ ID NO 1
<211> LENGTH: 355
<212> TYPE: PRT

```
<213> ORGANISM: Homo sapien

<400> SEQUENCE: 1

Met Glu Thr Pro Asn Thr Thr Glu Asp Tyr Asp Thr Thr Thr Glu Phe
 1               5                  10                  15

Asp Tyr Gly Asp Ala Thr Pro Cys Gln Lys Val Asn Glu Arg Ala Phe
            20                  25                  30

Gly Ala Gln Leu Leu Pro Pro Leu Tyr Ser Leu Val Phe Val Ile Gly
            35                  40                  45

Leu Val Gly Asn Ile Leu Val Val Leu Val Leu Val Gln Tyr Lys Arg
    50                  55                  60

Leu Lys Asn Met Thr Ser Ile Tyr Leu Leu Asn Leu Ala Ile Ser Asp
65                  70                  75                  80

Leu Leu Phe Leu Phe Thr Leu Pro Phe Trp Ile Asp Tyr Lys Leu Lys
                85                  90                  95

Asp Asp Trp Val Phe Gly Asp Ala Met Cys Lys Ile Leu Ser Gly Phe
                100                 105                 110

Tyr Tyr Thr Gly Leu Tyr Ser Glu Ile Phe Phe Ile Ile Leu Leu Thr
            115                 120                 125

Ile Asp Arg Tyr Leu Ala Ile Val His Ala Val Phe Ala Leu Arg Ala
    130                 135                 140

Arg Thr Val Thr Phe Gly Val Ile Thr Ser Ile Ile Ile Trp Ala Leu
145                 150                 155                 160

Ala Ile Leu Ala Ser Met Pro Gly Leu Tyr Phe Ser Lys Thr Gln Trp
                165                 170                 175

Glu Phe Thr His His Thr Cys Ser Leu His Phe Pro His Glu Ser Leu
                180                 185                 190

Arg Glu Trp Lys Leu Phe Gln Ala Leu Lys Leu Asn Leu Phe Gly Leu
            195                 200                 205

Val Leu Pro Leu Leu Val Met Ile Ile Cys Tyr Thr Gly Ile Ile Lys
    210                 215                 220

Ile Leu Leu Arg Arg Pro Asn Glu Lys Lys Ser Lys Ala Val Arg Leu
225                 230                 235                 240

Ile Phe Val Ile Met Ile Ile Phe Phe Leu Phe Trp Thr Pro Tyr Asn
                245                 250                 255

Leu Thr Ile Leu Ile Ser Val Phe Gln Asp Phe Leu Phe Thr His Glu
            260                 265                 270

Cys Glu Gln Ser Arg His Leu Asp Leu Ala Val Gln Val Thr Glu Val
            275                 280                 285

Ile Ala Tyr Thr His Cys Cys Val Asn Pro Val Ile Tyr Ala Phe Val
    290                 295                 300

Gly Glu Arg Phe Arg Lys Tyr Leu Arg Gln Leu Phe His Arg Arg Val
305                 310                 315                 320

Ala Val His Leu Val Lys Trp Leu Pro Phe Leu Ser Val Asp Arg Leu
                325                 330                 335

Glu Arg Val Ser Ser Thr Ser Pro Ser Thr Gly Glu His Glu Leu Ser
            340                 345                 350

Ala Gly Phe
        355
```